United States Patent
Backfish et al.

(10) Patent No.: US 11,865,316 B2
(45) Date of Patent: Jan. 9, 2024

(54) MEDICATION DELIVERY DEVICE INCLUDING DISPOSABLE AND REUSABLE PORTIONS

(71) Applicant: Eli Lilly and Company, Indianapolis, IN (US)

(72) Inventors: Matthew David Backfish, Zionsville, IN (US); Murat Günay, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/246,589

(22) PCT Filed: Oct. 22, 2021

(86) PCT No.: PCT/US2021/056126
§ 371 (c)(1),
(2) Date: Mar. 24, 2023

(87) PCT Pub. No.: WO2022/087325
PCT Pub. Date: Apr. 28, 2022

(65) Prior Publication Data
US 2023/0310753 A1 Oct. 5, 2023

Related U.S. Application Data

(60) Provisional application No. 63/104,544, filed on Oct. 23, 2020.

(51) Int. Cl.
*A61M 5/315* (2006.01)
*A61M 5/28* (2006.01)

(52) U.S. Cl.
CPC .......... *A61M 5/31575* (2013.01); *A61M 5/28* (2013.01); *A61M 2005/3152* (2013.01);
(Continued)

(58) Field of Classification Search
CPC ............... A61M 5/31575; A61M 5/28; A61M 2005/31518; A61M 2005/3152; A61M 2005/31588; A61M 2005/14268
See application file for complete search history.

(56) References Cited

U.S. PATENT DOCUMENTS

| 5,807,334 A | * | 9/1998 | Hodosh | A61M 5/482 604/224 |
|---|---|---|---|---|
| 9,579,459 B2 | | 2/2017 | Jennings et al. | |

(Continued)

FOREIGN PATENT DOCUMENTS

| WO | 2013074344 | 5/2013 |
|---|---|---|
| WO | 2019158372 | 8/2019 |

OTHER PUBLICATIONS

Patent Cooperation Treaty International Search Report of the International Searching Authority pertaining to International Application No. PCT/US2021/056126; International Filing Date: Oct. 22, 2021; dated Feb. 9, 2022.

(Continued)

*Primary Examiner* — Tasnim Mehjabin Ahmed
(74) *Attorney, Agent, or Firm* — M. Daniel Spillman

(57) ABSTRACT

A medication delivery device includes a disposable portion and a reusable portion. The disposable portion includes a therapeutic agent delivery assembly, and the therapeutic agent delivery assembly includes a needle. The therapeutic agent delivery assembly is translatable from a stowed configuration to a deployed configuration. The reusable portion includes a first rack and pinion mechanism and a second rack and pinion mechanism. The first rack and pinion mechanism is actuatable to translate the therapeutic agent delivery assembly from the stowed configuration to the deployed configuration. The second rack and pinion mechanism is actuatable to translate a plunger and thereby cause the (Continued)

therapeutic agent delivery assembly to deliver a therapeutic agent from the needle.

20 Claims, 21 Drawing Sheets

(52) U.S. Cl.
CPC ............ *A61M 2005/31518* (2013.01); *A61M 2005/31588* (2013.01)

(56) References Cited

U.S. PATENT DOCUMENTS

| | | | |
|---|---|---|---|
| 9,623,180 | B2 | 4/2017 | Iio et al. |
| 9,707,354 | B2 | 7/2017 | Madsen et al. |
| 9,849,252 | B2 | 12/2017 | Armes |
| 10,092,706 | B2 | 10/2018 | Denzer et al. |
| 10,149,947 | B2 | 12/2018 | Bayer et al. |
| 10,384,007 | B2 | 8/2019 | Henderson et al. |
| 10,492,990 | B2 | 12/2019 | Mounce et al. |
| 10,518,033 | B2 | 12/2019 | Takabatake et al. |
| 2013/0267897 | A1 | 10/2013 | Kemp et al. |
| 2013/0274655 | A1* | 10/2013 | Jennings ............ A61M 5/3213 604/152 |
| 2016/0354556 | A1 | 12/2016 | Zucker et al. |
| 2018/0353696 | A1 | 12/2018 | Helmer et al. |

OTHER PUBLICATIONS

Patent Cooperation Treaty Written Opinion of the International Searching Authority pertaining to International Application No. PCT/US2021/056126; International Filing Date: Oct. 22, 2021; dated Feb. 9, 2022.

* cited by examiner

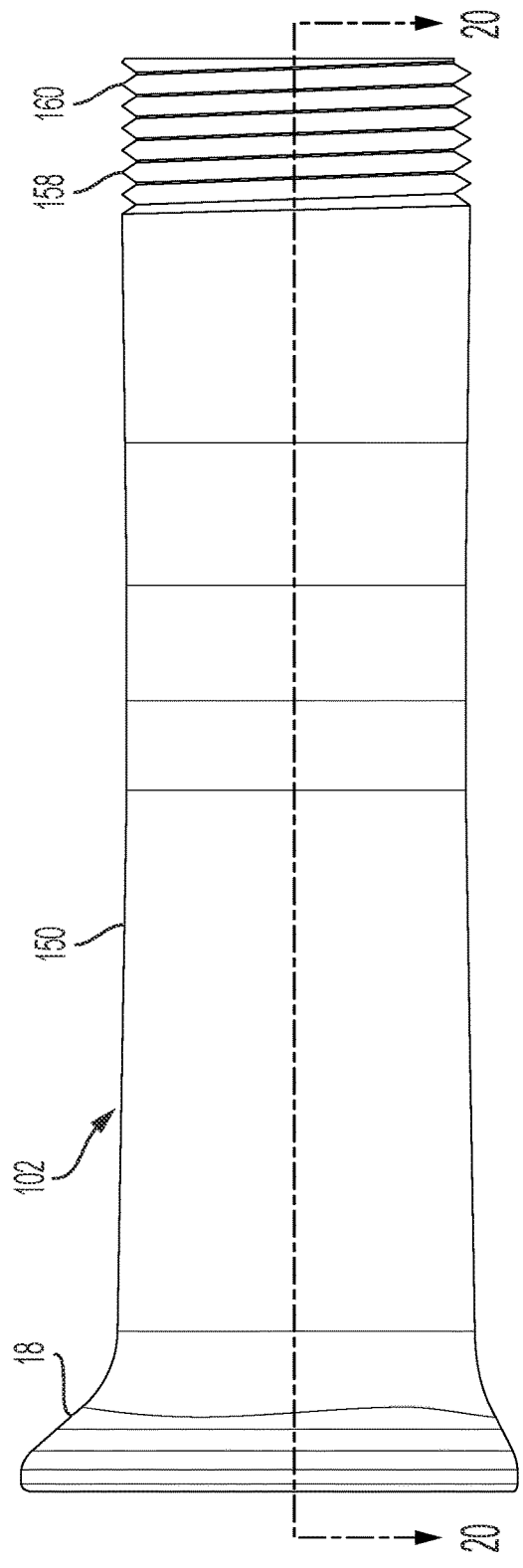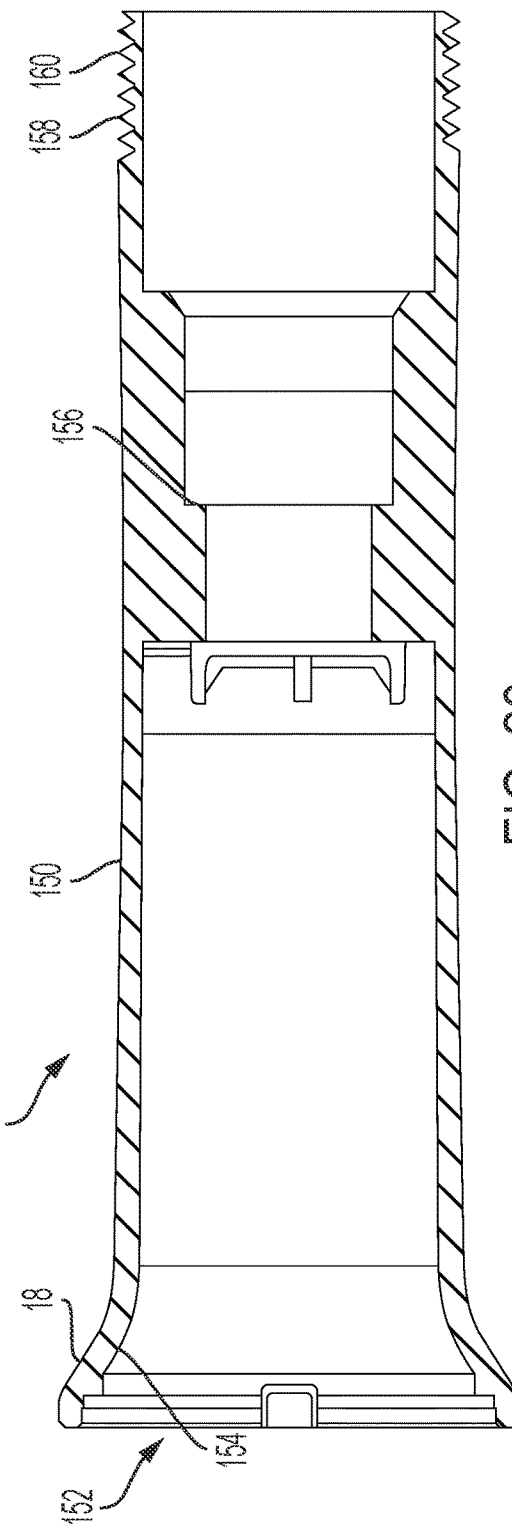
FIG. 19
FIG. 20

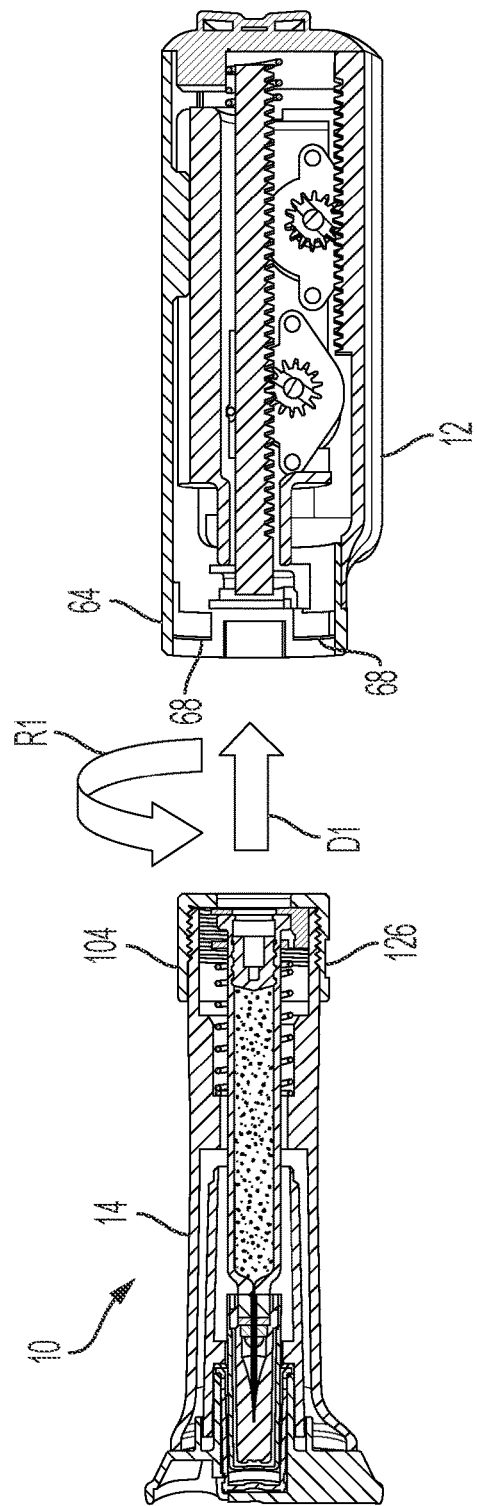
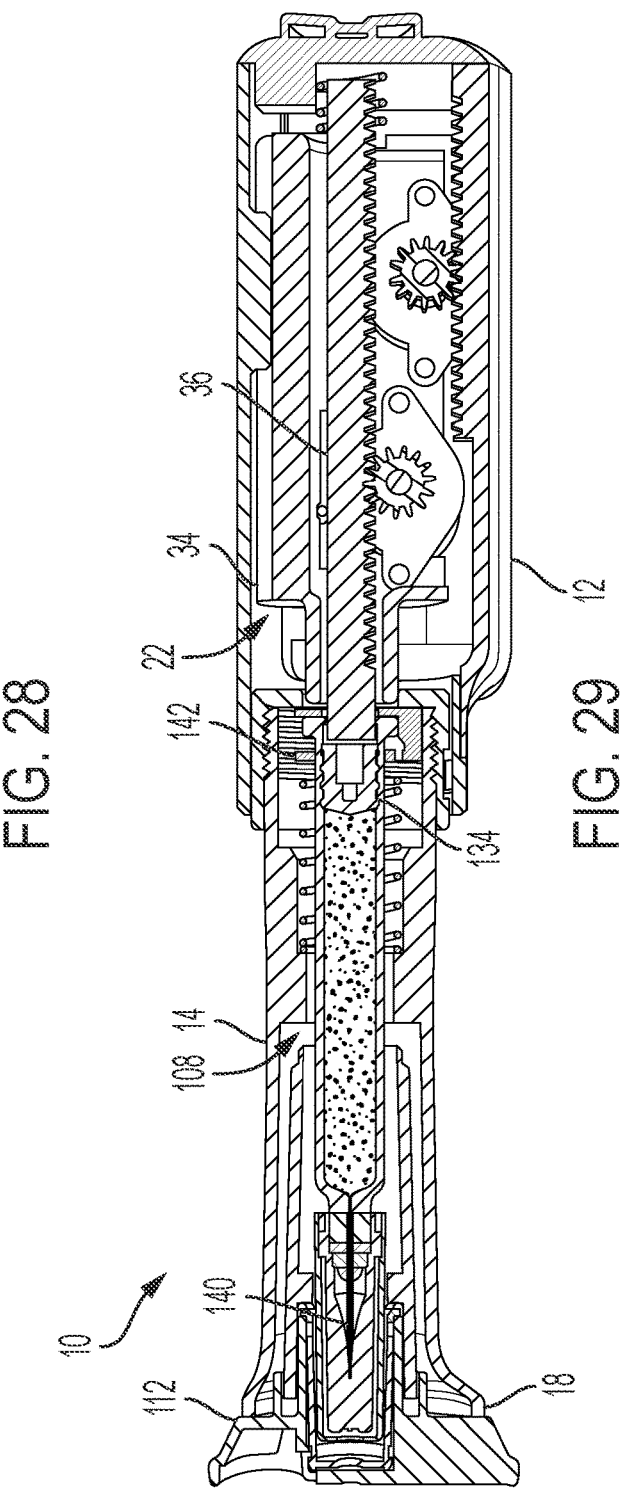
FIG. 28
FIG. 29

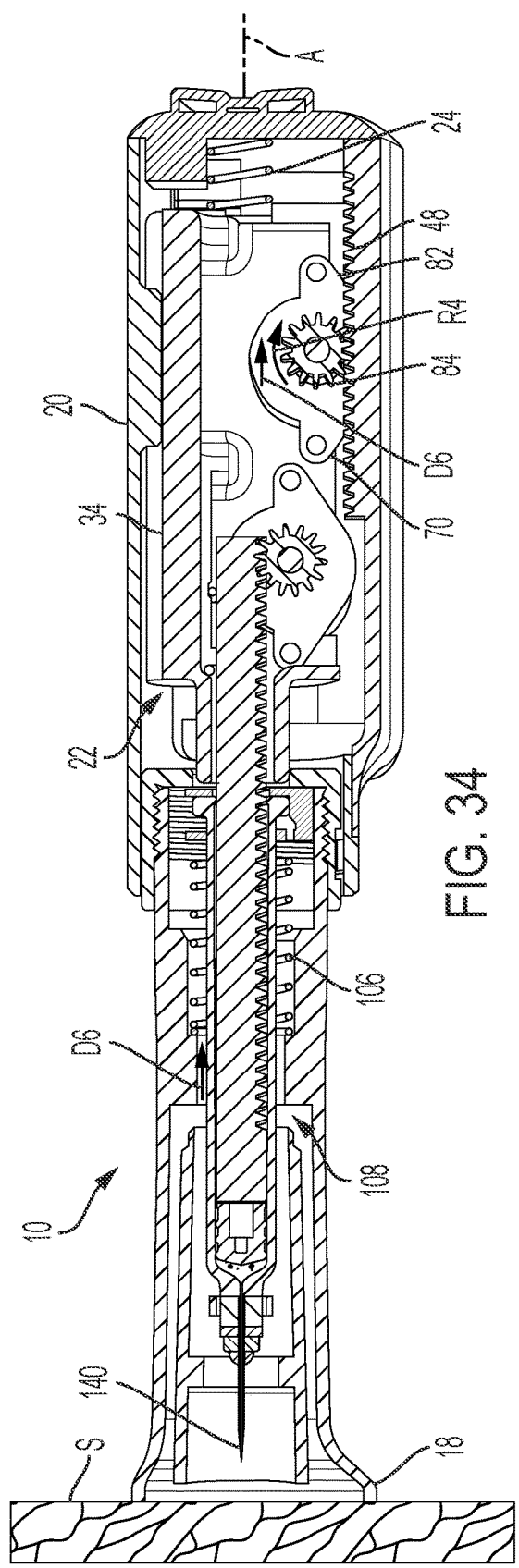
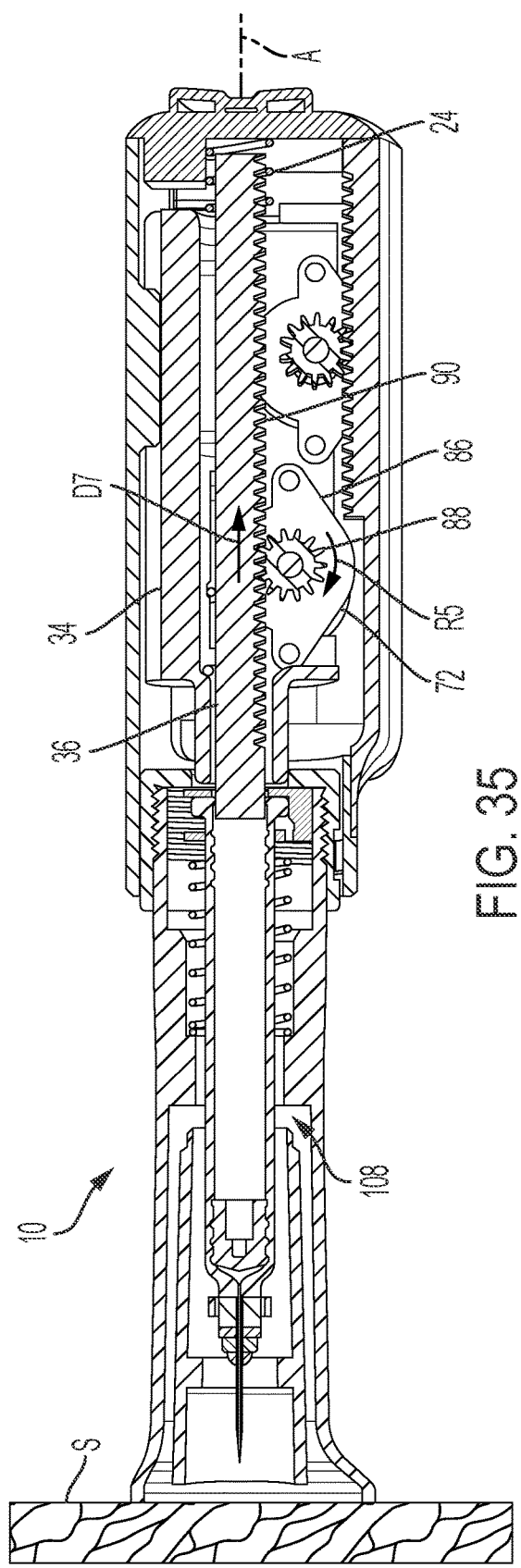
FIG. 34
FIG. 35

MEDICATION DELIVERY DEVICE INCLUDING DISPOSABLE AND REUSABLE PORTIONS

BACKGROUND

The present disclosure pertains to medication delivery devices, and, in particular, to a portable medication delivery device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and one or more doses of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable pens, after a pen has been used and exhausted the supply of medication within the cartridge, the entire pen is discarded by a user, who may then begin using a replacement pen. In reusable pens, after a pen has been used and exhausted the supply of medication within the cartridge, the pen is disassembled, the spent cartridge is replaced with a fresh cartridge, and the pen is reassembled for its subsequent use.

It would be desirable to provide a medication delivery device with improved features, such as a providing a reusable device that facilitates ease of replacement of a spent cartridge with a fresh cartridge and reduces the size and/or the number of components of the spent cartridge to reduce waste.

SUMMARY

According to an embodiment of the present disclosure, a medication delivery device is provided. The medication delivery device includes a disposable portion and a reusable portion. The disposable portion includes a housing having a distal end and a therapeutic agent delivery assembly carried by the housing. The therapeutic agent delivery assembly includes a chamber including a passageway, a therapeutic agent carried in the passageway, and a needle in communication with the passageway. The therapeutic agent delivery assembly is translatable relative to the housing from a stowed configuration to a deployed configuration, in the stowed configuration the needle is disposed proximally relative to the distal end of the housing, and in the deployed configuration the needle at least partially extends distally from the distal end of the housing. The reusable portion includes a housing and a drive mechanism carried by the housing of the reusable portion. The drive mechanism includes a first rack and pinion mechanism and a frame translatably carried by the housing of the reusable portion via the first rack and pinion mechanism. The drive mechanism further includes a second rack and pinion mechanism coupled to the frame and a plunger translatably carried by the frame via the second rack and pinion mechanism. The first rack and pinion mechanism is actuatable to translate the frame relative to the housing of the reusable portion, and the frame thereby translates the therapeutic agent delivery assembly relative to the housing of the disposable portion from the stowed configuration to the deployed configuration. The second rack and pinion mechanism is actuatable to translate the plunger relative to the frame, the plunger thereby causes the therapeutic agent delivery assembly to deliver the therapeutic agent from the needle.

According to another embodiment of the present disclosure, a method for delivering a therapeutic agent from a medication delivery device to a patient is provided. The medication delivery device includes a reusable portion and a disposable portion that is detachably carried by the reusable portion, and the disposable portion carries the therapeutic agent. The method includes positioning a distal end of the disposable portion adjacent to the skin of the patient, and a needle of the disposable portion is disposed proximally relative to the distal end of the disposable portion. The method further includes actuating a first rack and pinion mechanism of the reusable portion to thereby drive the needle relative to the distal end of the disposable portion such that the needle at least partially extends distally from the distal end of the disposable portion and pierces the skin of the patient. The method further includes actuating a second rack and pinion mechanism of the reusable portion to thereby cause the disposable portion to deliver the therapeutic agent from the needle to the patient.

According to yet another embodiment of the present disclosure, a disposable portion for a medication delivery device is provided. The medication delivery device includes a reusable portion that is configured to detachably carry the disposable portion. The disposable portion includes a housing having a distal end and a therapeutic agent delivery assembly translatably carried in the housing. The therapeutic agent delivery assembly includes a chamber having a passageway, a therapeutic agent carried in the passageway, and a needle in communication with the passageway. A biasing element is carried in the housing, and the biasing element biases the therapeutic agent delivery assembly toward a stowed configuration. In the stowed configuration the needle is disposed proximally relative to the distal end of the housing. A proximal cover is carried by the housing. The proximal cover retains the therapeutic agent delivery assembly in the housing, and the proximal cover includes a securing feature that is configured to detachably secure the disposable portion to the reusable portion. The therapeutic agent delivery assembly is translatable by the reusable portion relative to the housing from the stowed configuration to a deployed configuration. In the deployed configuration the needle at least partially extends distally from the distal end of the housing.

According to yet another embodiment of the present disclosure, a drive portion of a medication delivery device is provided. The drive portion includes a housing and a drive mechanism carried by the housing. The drive mechanism includes a first rack and pinion mechanism, and a frame translatably carried by the housing via the first rack and pinion mechanism. Also includes is a second rack and pinion mechanism coupled to the frame, and a plunger translatably carried by the frame via the second rack and pinion mechanism. The first rack and pinion mechanism is actuatable to translate the frame relative to the housing configured to translate a therapeutic agent delivery assembly from a stowed configuration to a deployed configuration. The second rack and pinion mechanism is actuatable to translate the plunger relative to the frame to deliver a therapeutic agent from a needle of the therapeutic agent delivery assembly.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIG. 19 is a side view of a housing of the disposable portion of FIG. 13.

FIG. 20 is a longitudinal sectional view of the housing along line 20-20 of FIG. 19.

FIG. 28 is a longitudinal sectional view of the medication delivery device of FIG. 1 before coupling the disposable portion to the reusable portion.

FIG. 29 is a longitudinal sectional view of the medication delivery device of FIG. 1 upon coupling the disposable portion to the reusable portion.

FIG. 34 is a longitudinal sectional view of the medication delivery device of FIG. 1 upon retracting the needle from the patient.

FIG. 35 is a longitudinal sectional view of the medication delivery device of FIG. 1 upon retracting the plunger from the therapeutic agent delivery assembly.

Figure 1:
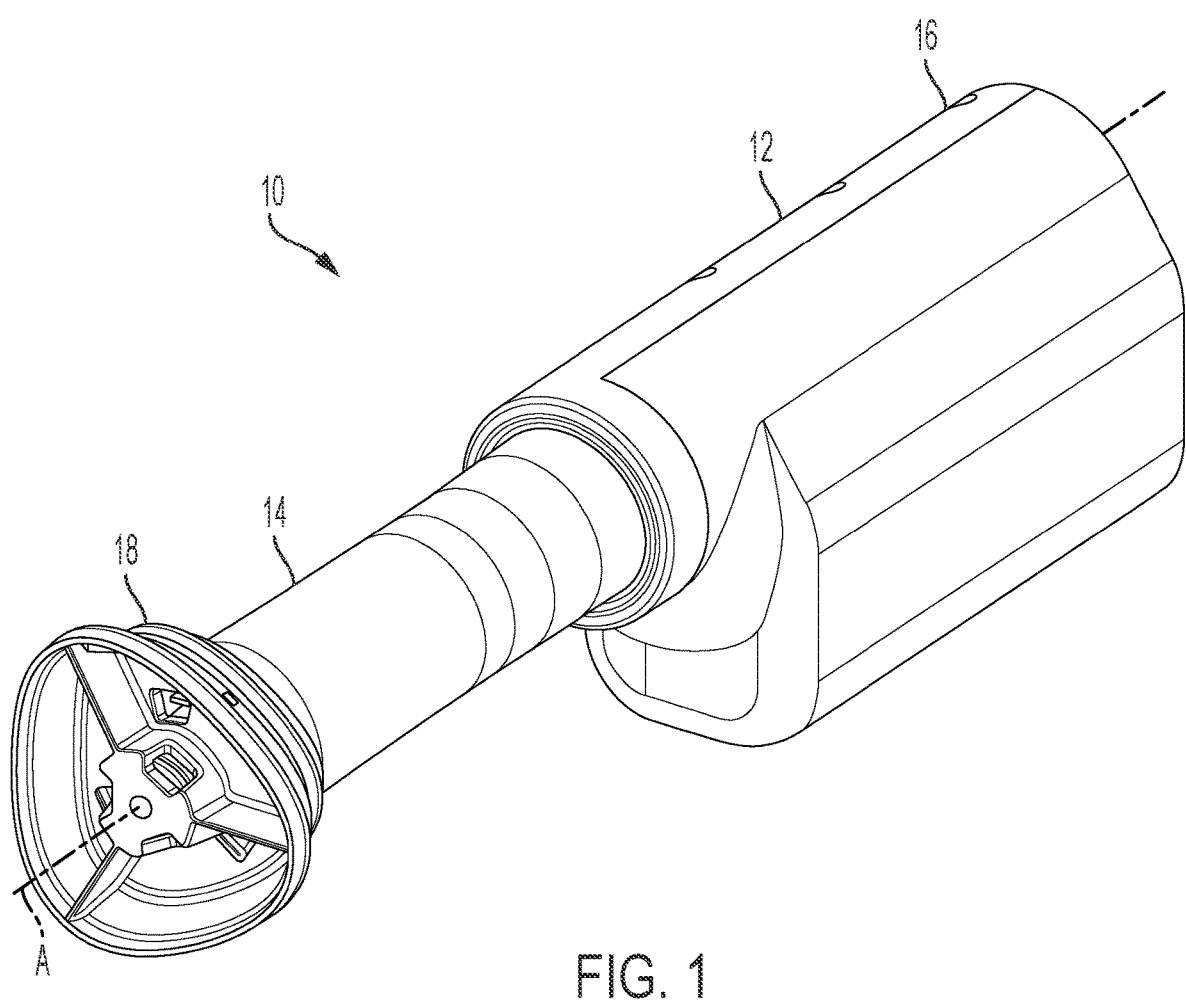
FIG. 1 is a perspective view of a medication delivery device according to an embodiment of the present disclosure.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Any directional references used with respect to any of the Figures, such as right or left, up or down, or top or bottom, are intended for convenience of description, and does not limit the present disclosure or any of its components to any particular positional or spatial orientation.

Figure 2:
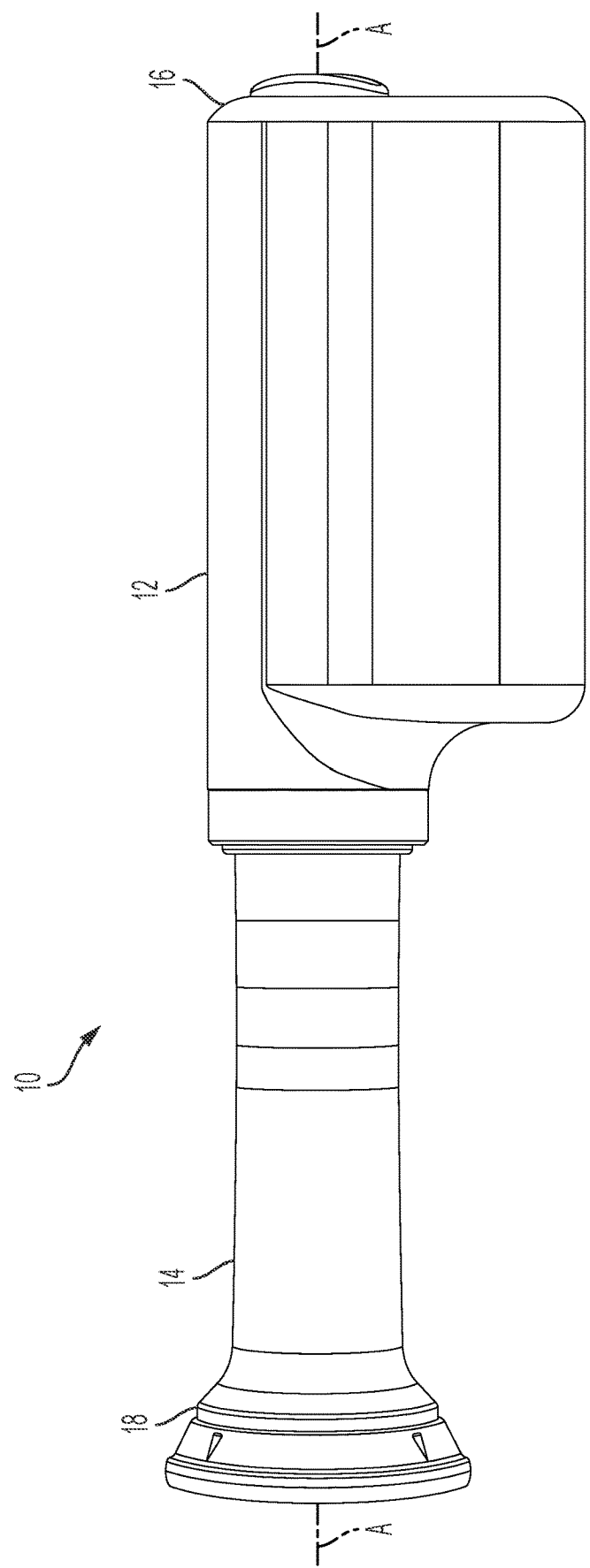
FIG. 2 is a side view of the medication delivery device of FIG. 1.

FIGS. 1 and 2 illustrate a medication delivery device 10 according to an exemplary embodiment of the present disclosure. Illustratively, the medication delivery device 10 has an injector pen-like shape, although other shapes may alternatively be used. The medication delivery device 10 generally includes a reusable portion 12, which may also be referred to as a drive portion, and a disposable portion 14, which may also be referred to as a drug carrying portion. The reusable portion 12 facilitates delivery of a therapeutic agent (shown elsewhere) from the disposable portion 14. In addition, the reusable portion 12 detachably couples to the disposable portion 14 such that after the therapeutic agent has been delivered from the disposable portion 14, the disposable portion 14 may be detached from the reusable portion 12 and discarded. Another disposable portion (not shown—for example, having the same or different features than the disposable portion 14) may then be attached to the reusable portion 12, and the medication delivery device 10 is thereby ready for subsequent use. In one embodiment, the reusable portion 12 and the disposable portion 14 may be permanently secured to one another to define a disposable device.

The medication delivery device 10 also includes a proximal end 16 and an opposite distal end 18. During use of the medication delivery device 10, the proximal end 16 would be farther from the patient and configured to be actuated by the user, and the distal end 18 would be closer to the patient and configured to deliver the therapeutic agent (shown elsewhere) to the patient. The medication delivery device 10 also includes a longitudinal axis A extending between the proximal end 16 and the distal end 18. These and other features of the medication delivery device 10 are described in further detail below.

Figure 3:
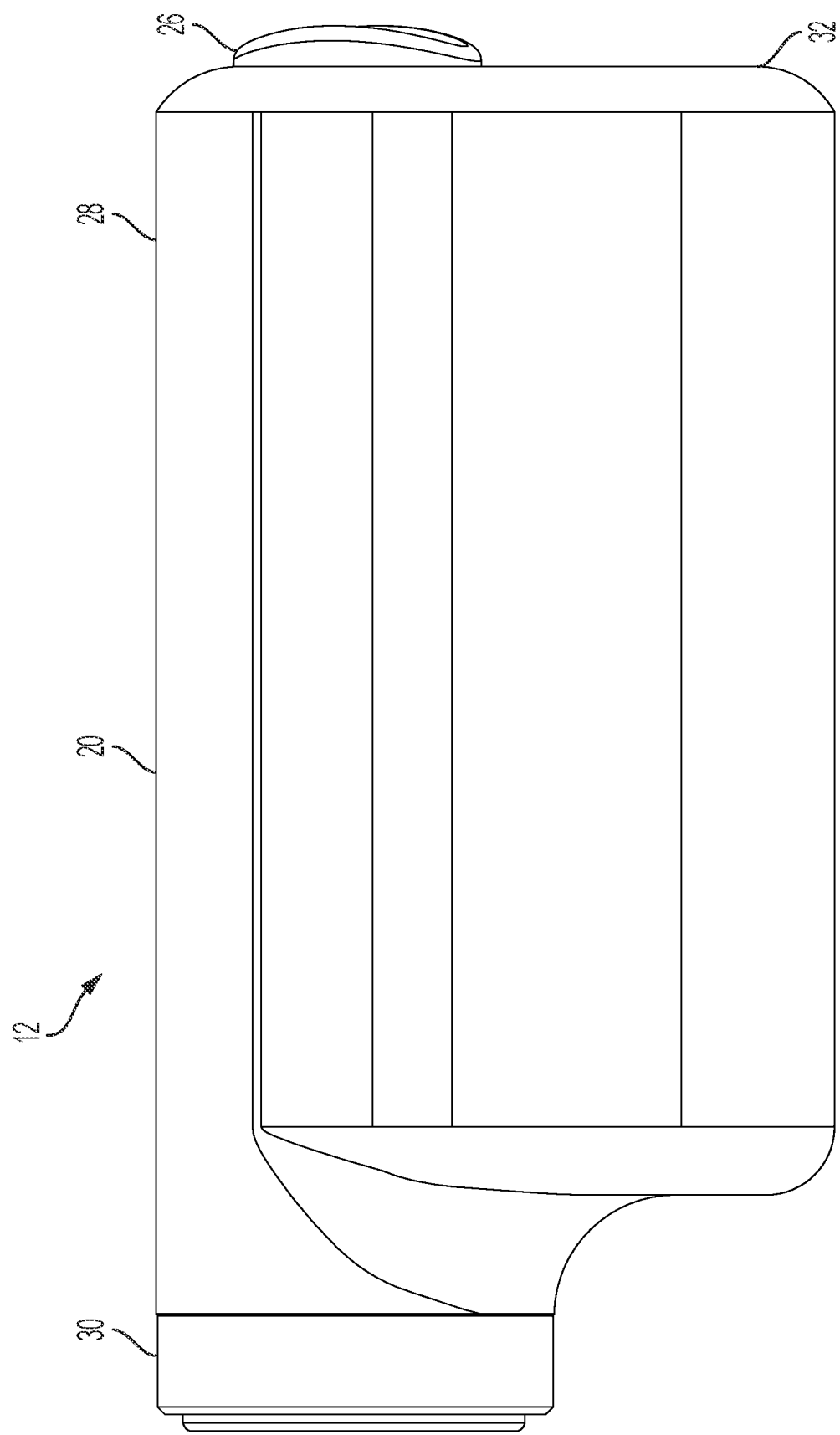
FIG. 3 is a side view of a reusable portion of the medication delivery device of FIG. 1.
Figure 4:
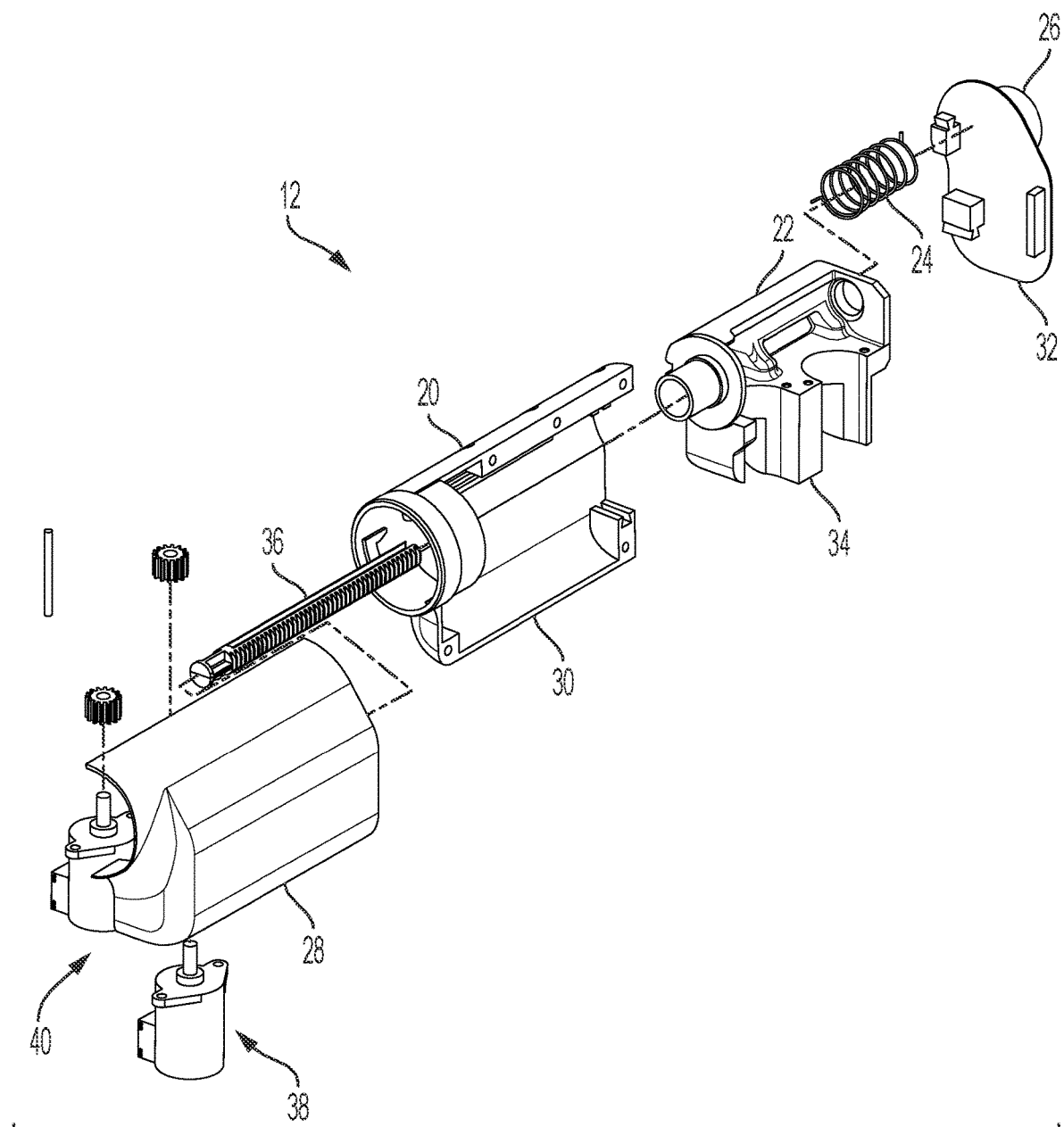
FIG. 4 is an exploded perspective view of the reusable portion of FIG. 3.

FIGS. 3 and 4 illustrate the reusable portion 12 of the medication delivery device 10. With specific reference to the exploded view of FIG. 4, the reusable portion 12 generally includes a housing 20 that carries a drive mechanism 22, a biasing element 24 (illustratively, a compression spring), and a user input or button 26. The reusable portion 12 further includes an electronics assembly (shown elsewhere) that facilitates actuating the drive mechanism 22.

The housing 20 illustratively includes a first housing portion 28 and a second housing portion 30 that carry the drive mechanism 22. The housing 20 further includes a third housing portion 32 that carries the user input 26. Illustratively, the drive mechanism 22 includes a frame 34 that is translatably carried by the housing 20 and a plunger 36 that is translatably carried by the frame 34. The drive mechanism 22 further includes a first rack and pinion mechanism 38 (only partially visible in FIG. 4) and a second rack and pinion mechanism 40. The first rack and pinion mechanism 38 and the second rack and pinion mechanism 40 are actuatable to drive the frame 34 relative to the housing 20 and the plunger 36 relative to the frame 34, respectively, to facilitate delivery of the therapeutic agent from the medication delivery device 10. The housing 20, the drive mechanism 22, and other features of the reusable portion 12 of the medication delivery device 10 are described in further detail below. In one embodiment the device includes one of the first or second rack and pinion mechanisms and another mechanism that is not a rack and pinion may be used for the syringe drive and plunger drive, such as a spring drive, a rotary or linear electric motor drive, chemical reaction drive, or the like.

Figure 5:
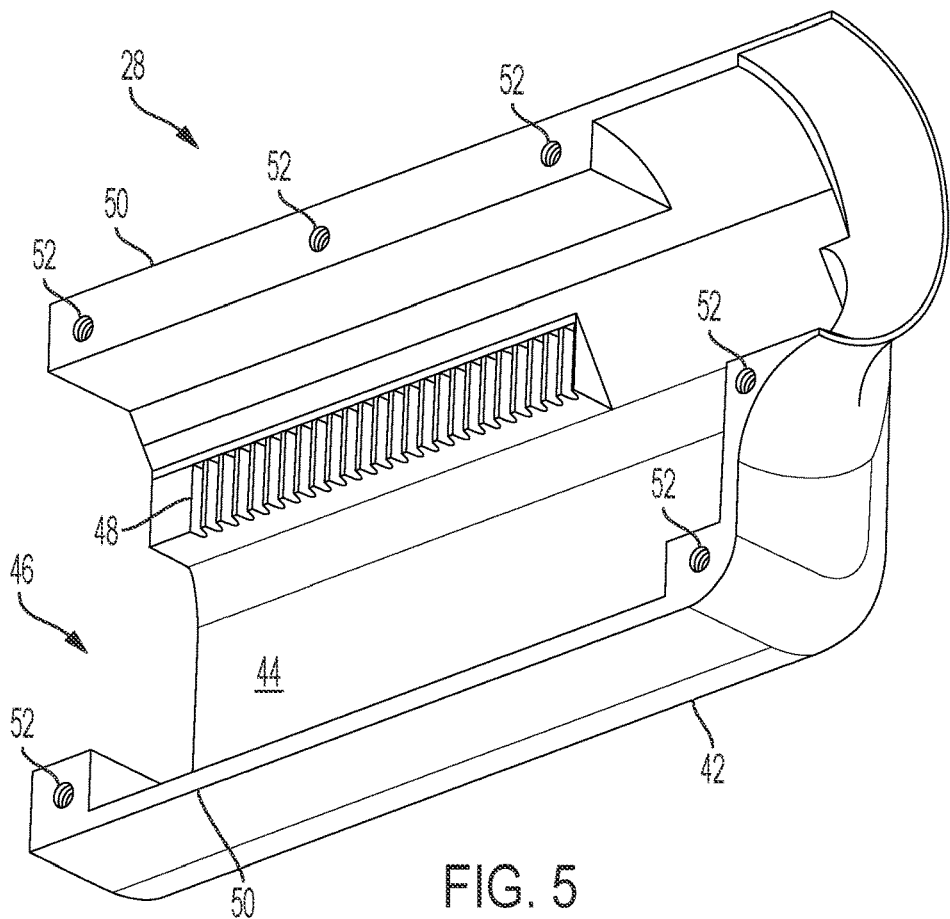
FIG. 5 is a perspective view of a first housing portion of the reusable portion of FIG. 3.
Figure 6:
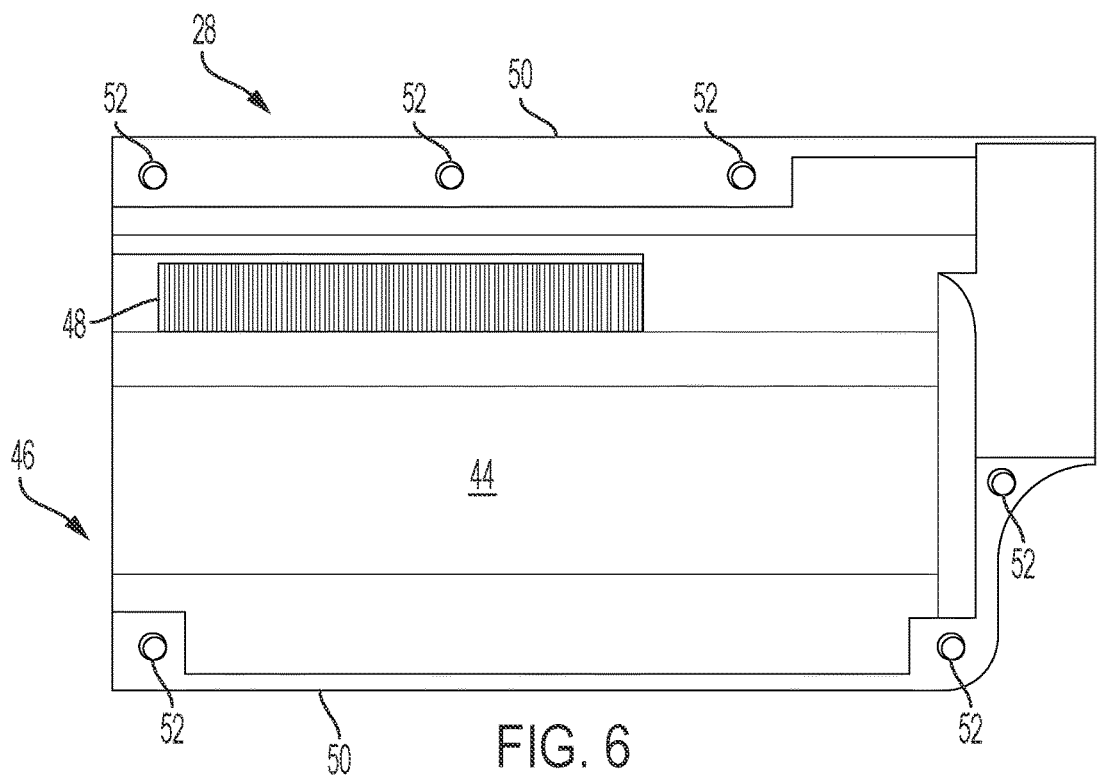
FIG. 6 is a side view of the first housing portion of FIG. 5.

FIGS. 5 and 6 illustrate the first housing portion 28 of the housing 20. The first housing portion 28 includes an external surface 42 and an opposite internal surface 44. The internal surface 44 partially defines an inner chamber 46 that receives the drive mechanism 22 (shown elsewhere). The internal surface 44 also defines a first rack 48 of the first rack and pinion mechanism 38 (shown elsewhere). Stated another way, the first housing portion 28 and the first rack 48 are monolithically formed with each other. The first housing portion 28 further includes upper and lower coupling surfaces 50 on opposite sides of the internal surface 44. The coupling surfaces 50 each include one or more coupling features 52 (illustratively, a plurality of threaded holes) that facilitate coupling the first housing portion 28 to the second housing portion 30 (shown elsewhere). In other embodiments, different arrangements of the first housing portion 28 are possible. For example, the first housing portion 28 and the first rack 48 may be formed separately, and the first rack 48 may be coupled to the internal surface 44 of the first housing portion 28 via, for example, one or more fasteners (not shown) and/or adhesives (not shown).

Figure 7:
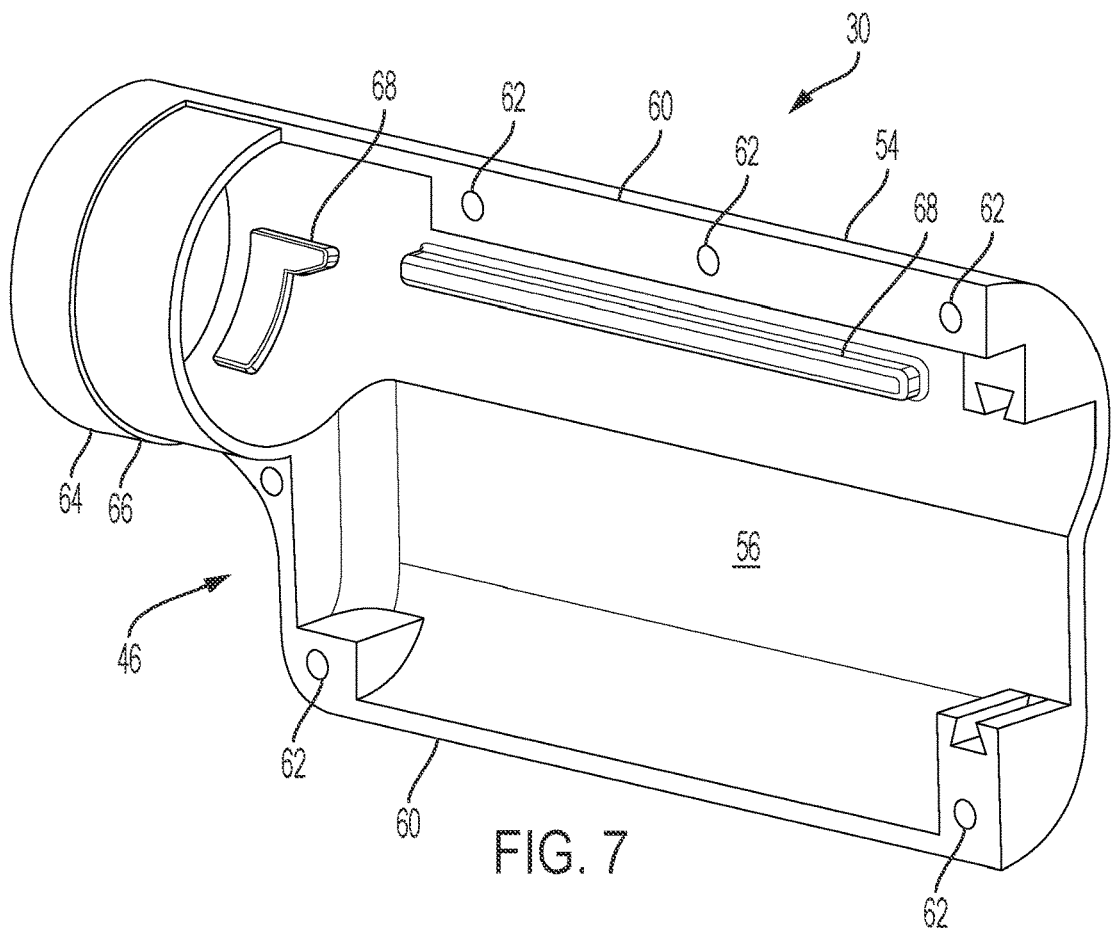
FIG. 7 is a perspective view of a second housing portion of the reusable portion of FIG. 3.
Figure 8:
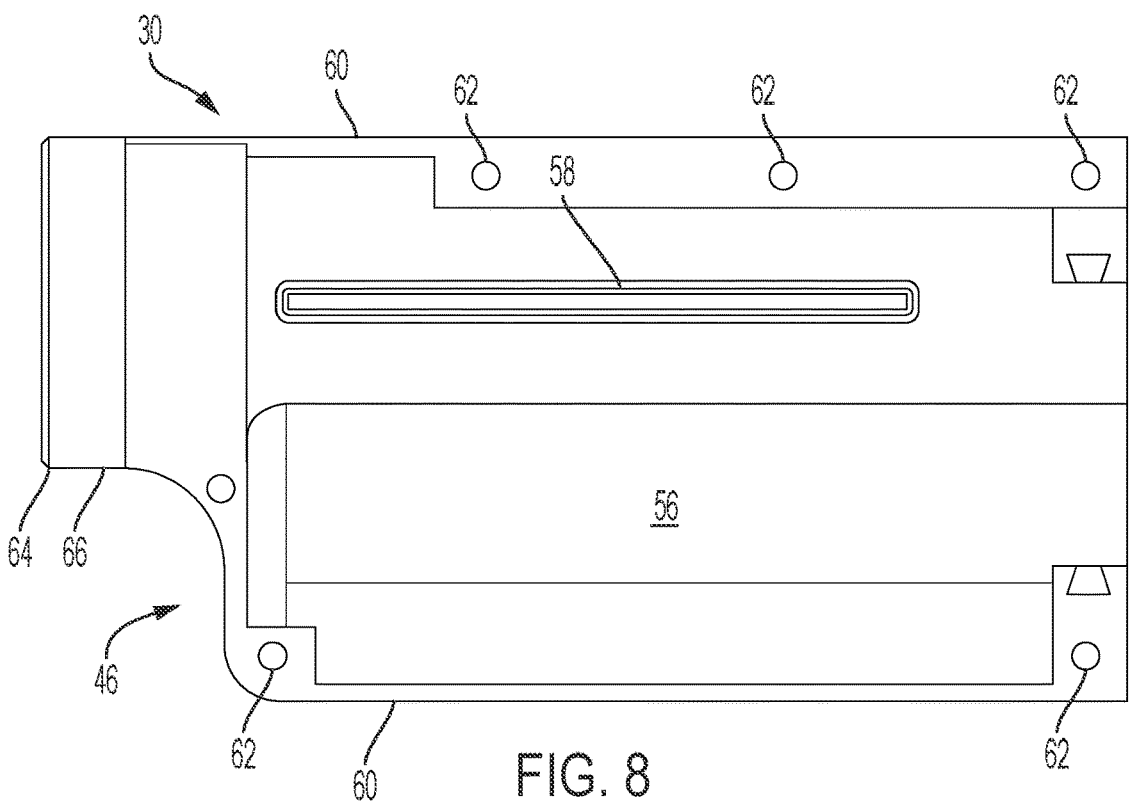
FIG. 8 is a side view of the second housing portion of FIG. 7.

FIGS. 7 and 8 illustrate the second housing portion 30 of the housing 20. The second housing portion 30 includes an external surface 54 and an opposite internal surface 56. The internal surface 56 defines, together with the first housing portion 28 (shown elsewhere), the inner chamber 46 that receives the drive mechanism 22 (shown elsewhere). The internal surface 56 also defines a translation feature 58 that facilitates translatably carrying the frame 34. Stated another way, the second housing portion 30 and the translation feature 58 are monolithically formed with each other. Illustratively, the translation feature 58 is provided as an elongated protrusion. The second housing portion 30 further includes upper and lower coupling surfaces 60 on opposite sides of the internal surface 56. The coupling surfaces 60 each include one or more coupling features 62 (illustratively, a plurality of apertures for receiving threaded fasteners—not shown) that facilitate coupling the second housing portion 30 to the first housing portion 28. The second housing portion 30 further includes a coupling portion 64 for detachably securing the reusable portion 12 to the disposable portion 14 (shown elsewhere). Illustratively, the coupling portion 64 includes a cylindrical wall 66 for receiving the disposable portion 14 and a plurality of securing features 68 (one of which is shown in FIG. 7) for securing the disposable portion 14 to the reusable portion 12. The securing features 68 may provide a bayonet-like or "twist-to-lock" connector; more specifically, the securing features 68 may be generally L-shaped protrusions. In other embodiments, different arrangements of the second housing portion 30 are possible. For example, the second housing portion 30 and the translation feature 58 may be formed separately, and the translation feature 58 may be coupled to the internal surface 56 of the second housing portion 30 via, for example, one or more fasteners (not shown) and/or adhesives (not shown). As another example, instead of providing the translation feature 58 as a positive feature (illustratively, the elongated protrusion), the translation feature 58 could be a negative feature (for example, an elongated slot—not shown). Other kinds of securing features 68 may be used, such as, for example, a flexing tab-in-slot connection, a threaded connection, a magnetic connection, or a key-in-slot connection.

Figure 9:
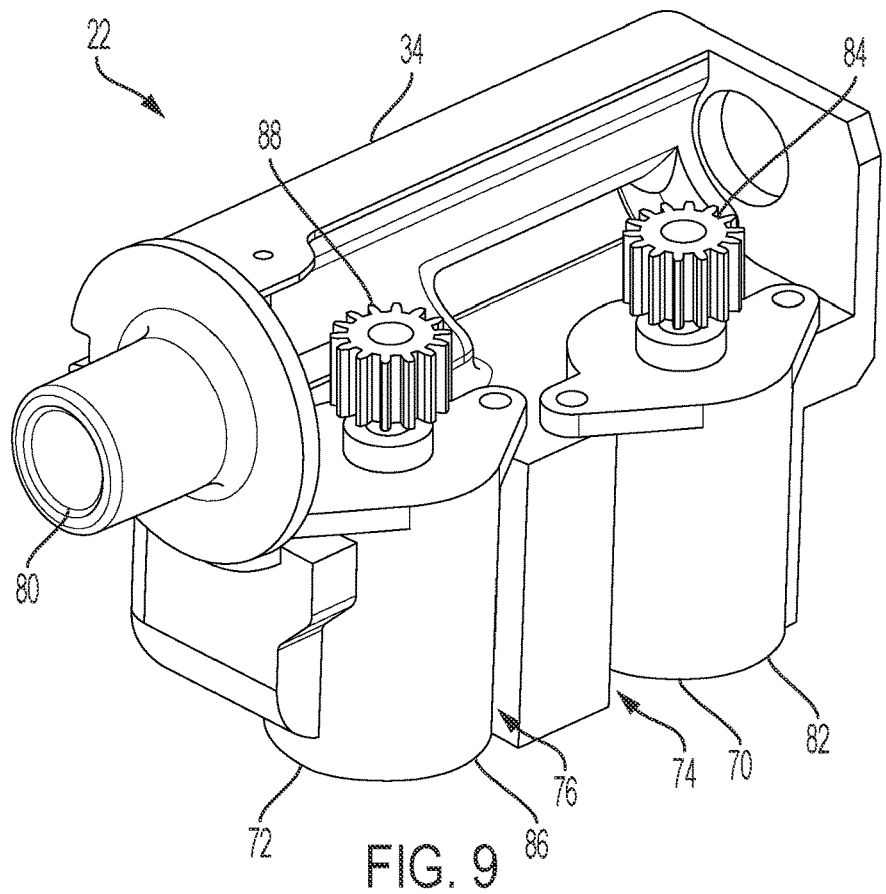
FIG. 9 is a perspective view of a frame and first and second actuators of the reusable portion of FIG. 3.
Figure 10:
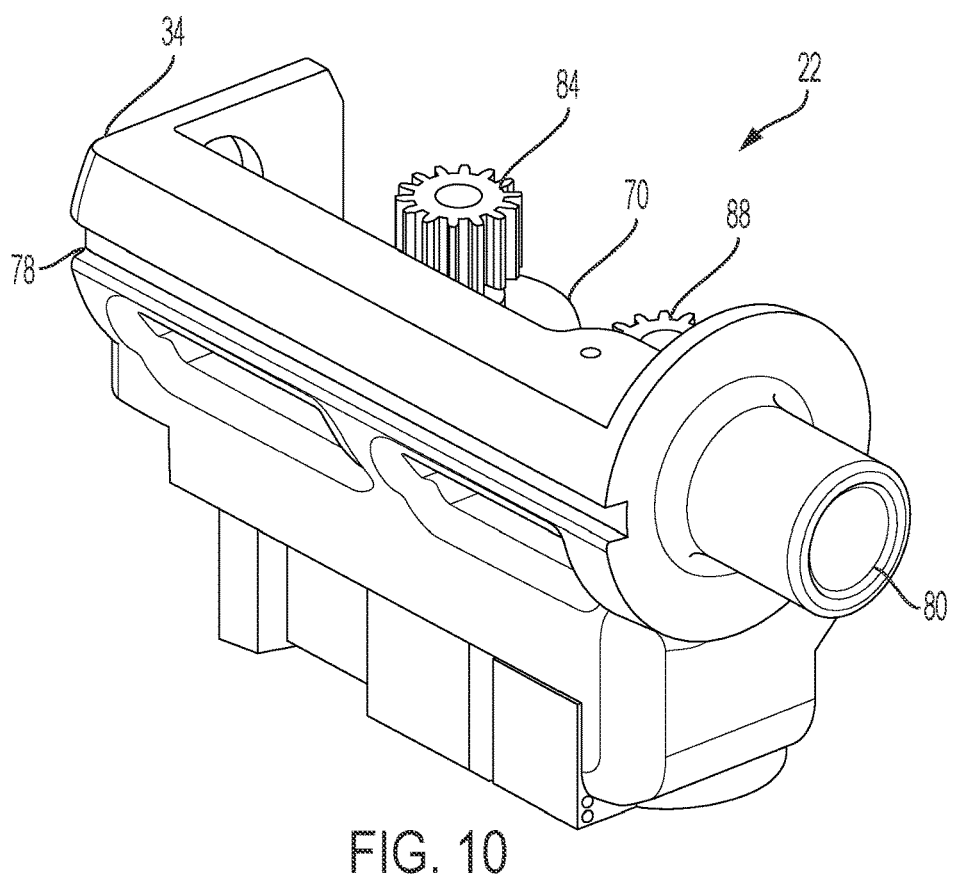
FIG. 10 is another perspective view of the frame and the first and second actuators of FIG. 9.

FIGS. 9 and 10 partially illustrate the drive mechanism 22 of the reusable portion 12 of the medication delivery device 10. More specifically, FIGS. 9 and 10 illustrate the frame 34, a first actuator 70 of the first rack and pinion mechanism 38 (shown elsewhere), and a second actuator 72 of the second rack and pinion mechanism 40 (shown elsewhere). The frame 34 includes a first mounting portion 74 that carries the first actuator 70 and a second mounting portion 76 that carries the second actuator 72. Opposite the first mounting portion 74 and the second mounting portion 76, the frame 34 further includes a translation feature 78 that couples to the translation feature 58 of the second housing portion 30 (shown elsewhere). Illustratively, the translation feature 58 is provided as an elongated slot. The frame 34 further includes a plunger aperture 80 that translatably receives the plunger 36 (shown elsewhere). In other embodiments, different arrangements of the frame 34 are possible. For example, instead of providing the translation feature 78 as a negative feature (illustratively, the elongated slot), the translation feature 78 could be a positive feature (for example, an elongated protrusion—not shown).

With continued referenced to FIGS. 9 and 10, the first actuator 70 includes a first motor 82 (for example, a stepper motor) that is carried by the first mounting portion 74 of the frame 34. The first actuator 70 further includes a first pinion 84 that is rotatably driven by energizing the first motor 82. The first pinion 84 drivingly engages the first rack 48 of the first rack and pinion mechanism 38 (shown elsewhere). As such, energizing the first motor 82 causes the first pinion 84 to rotate and drive the first rack 48, which causes the frame 34 to translate relative to the housing 20 (both shown elsewhere). Similarly, the second actuator 72 includes a second motor 86 (for example, a stepper motor) that is carried by the second mounting portion 76 of the frame 34. The second actuator 72 further includes a second pinion 88 that is rotatably driven by energizing the second motor 86. The second pinion 88 drivingly engages a second rack of the second rack and pinion mechanism 40 (shown elsewhere), which, as described in further detail below, is coupled to the plunger 36 (shown elsewhere). As such, energizing the second motor 86 causes the second pinion 88 to rotate and drive the second rack, which causes the plunger 36 to translate relative to the frame 34.

Figure 11:
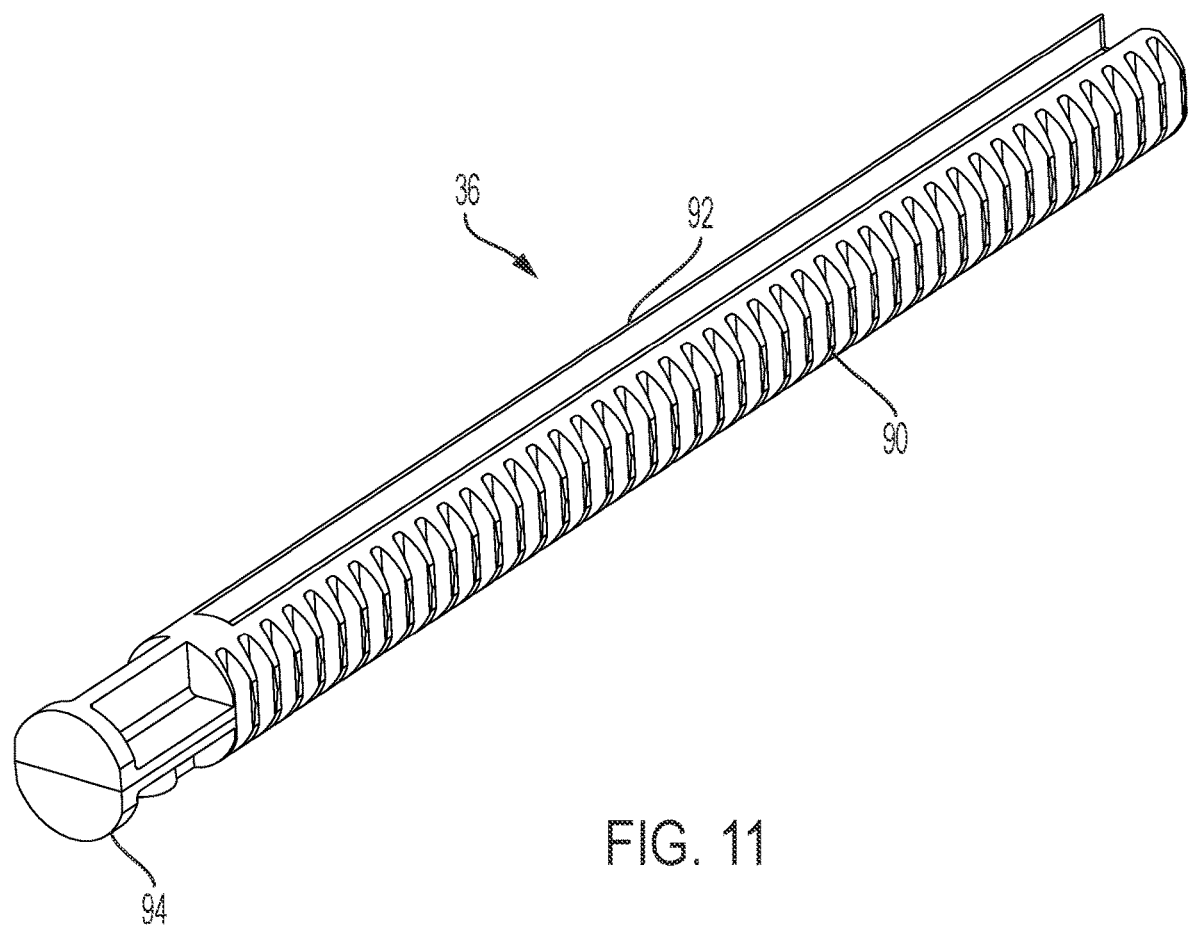
FIG. 11 is a perspective view of a plunger of the reusable portion of FIG. 3.

FIG. 11 illustrates the plunger 36 of the reusable portion 12 of the medication delivery device 10. The plunger 36 includes an elongated shaft 92, and a side of the shaft 92 defines the second rack 90 of the second rack and pinion mechanism 40 (shown elsewhere). Stated another way, the shaft 92 and the second rack 90 are monolithically formed with each other. The shaft 92 terminates at a distal end 94. The distal end 94 is configured to engage and actuate the disposable portion 14 (shown elsewhere) and thereby facilitate delivering the therapeutic agent from the disposable portion 14, as described in further detail below. In other embodiments, different arrangements of the plunger 36 are possible. For example, the plunger 36 and the second rack 90 may be formed separately, and the second rack 90 may be coupled to the plunger 36 via, for example, one or more fasteners (not shown) and/or adhesives (not shown).

Figure 12:
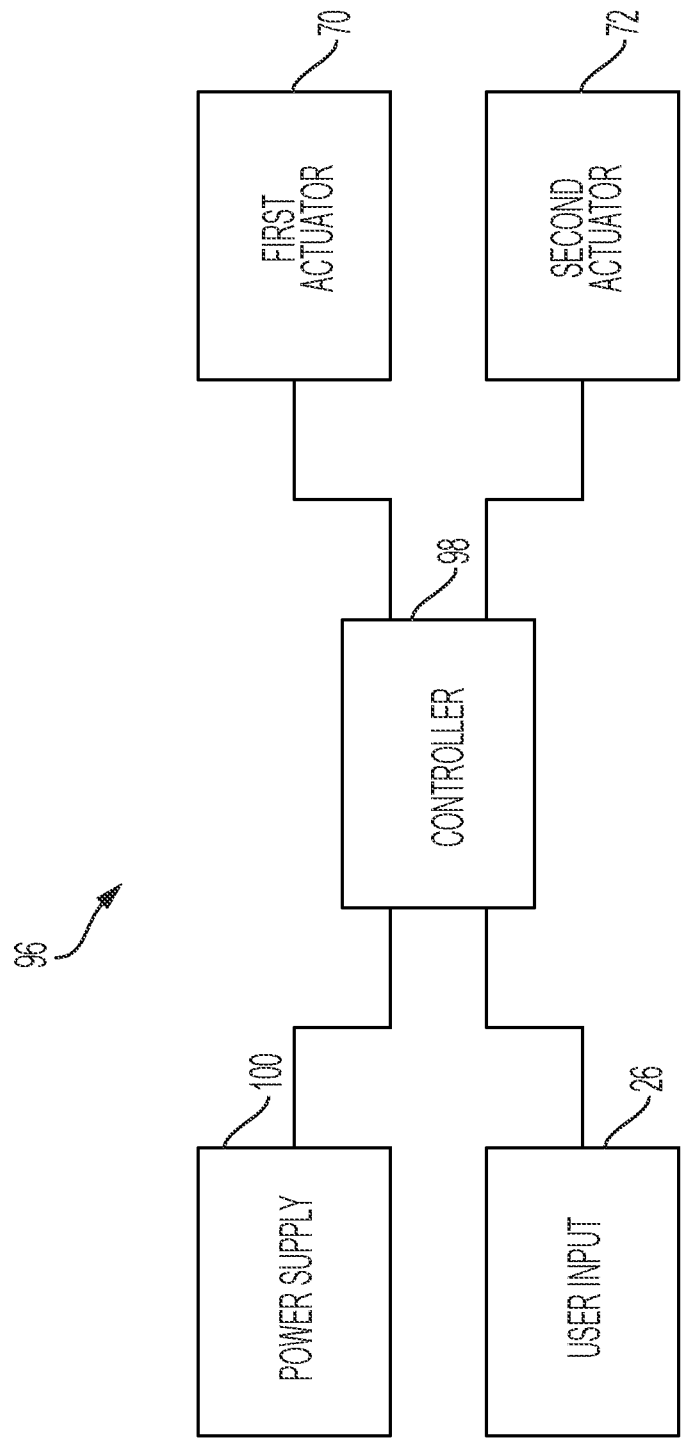
FIG. 12 is a schematic representation of an electronics assembly of the reusable portion of FIG. 3.

FIG. 12 illustrates the electronics assembly 96 of the reusable portion 12 of the medication delivery device 10. The electronics assembly 96 includes an electronic controller 98 that is operatively coupled to and receives power from a power supply 100 (illustratively, a battery). The electronic controller 98 operatively couples to the user input 26. Actuation of the user input 26 (for example, depressing the user input 26) may cause the user input 26 to send an actuation signal to the electronic controller 98 (for example, by closing an electrical circuit). The electronic controller 98 also operatively couples to the first actuator 70 and the second actuator 72. Upon receiving the actuation signal from the user input 26, the electronic controller 98 may energize the first actuator 70 and the second actuator 72 (for example, sequentially, as described in further detail below). In other embodiments, the electronics assembly 96 may take other forms. For example, the electronics assembly 96 and the electronic controller 98 may operatively couple to and receive power from an external power supply (not shown—for example, a wall outlet).

Figure 13:
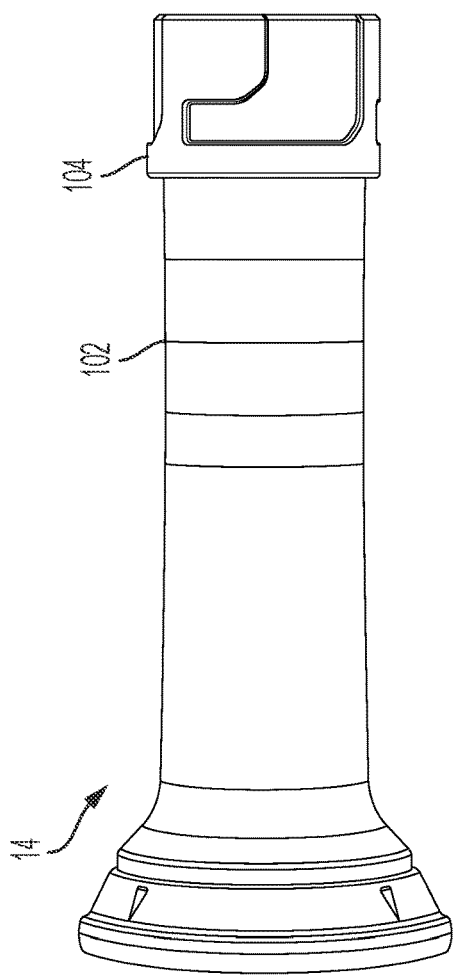
FIG. 13 is a side view of a disposable portion of the medication delivery device of FIG. 1.
Figure 14:
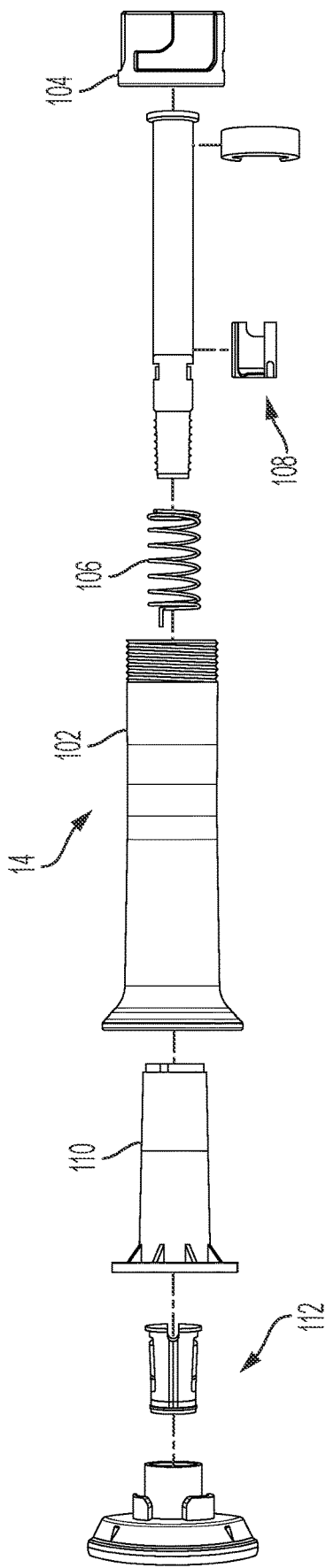
FIG. 14 is an exploded side view of the disposable portion of FIG. 13.

FIGS. 13 and 14 illustrate the disposable portion 14 of the medication delivery device 10. With specific reference to the exploded view of FIG. 14, the disposable portion 14 generally includes a housing 102 that carries a coupling element or proximal cover 104, a biasing element 106 (illustratively, a compression spring), a therapeutic agent delivery assembly 108, a baseplate 110, and a base portion 112.

Figure 15:
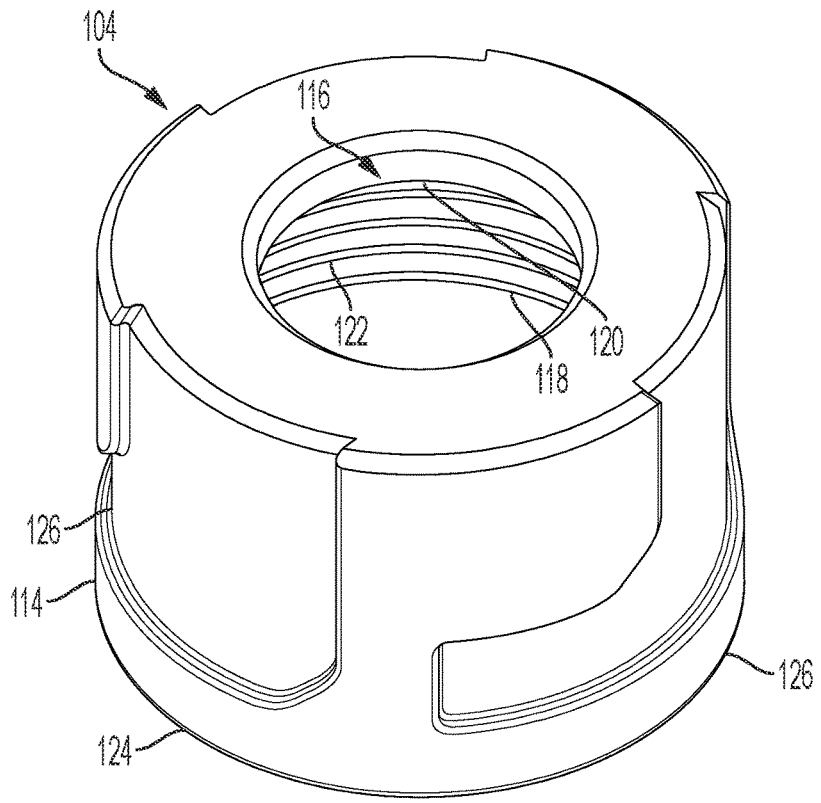
FIG. 15 is a top perspective view of a proximal cover of the of the disposable portion of FIG. 13.
Figure 16:
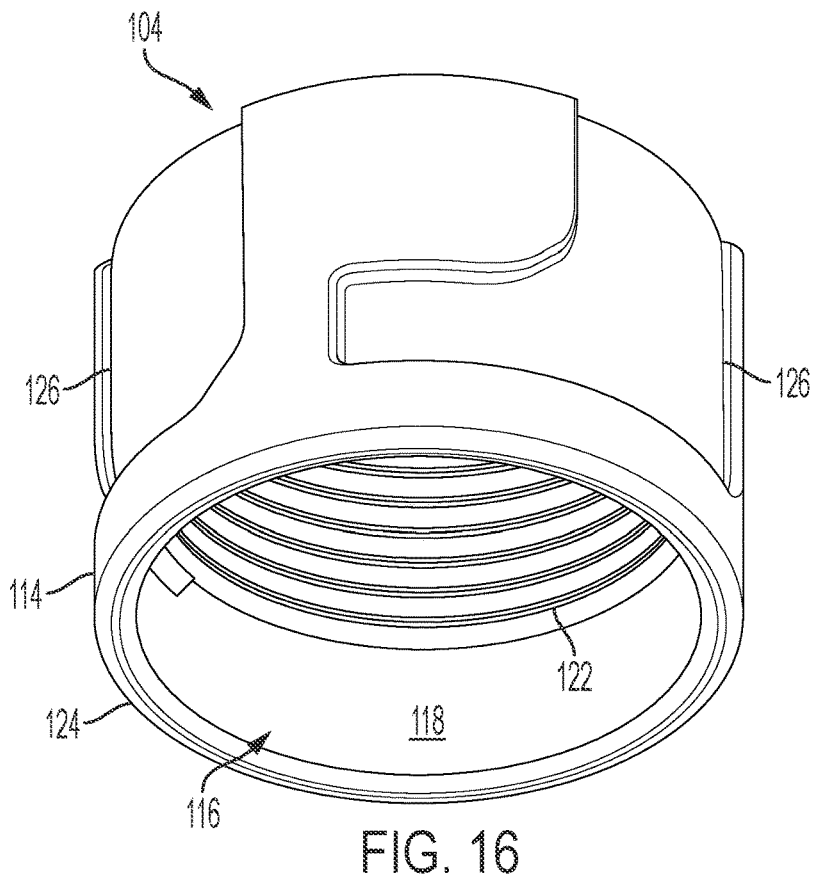
FIG. 16 is a bottom perspective view of the proximal cover of FIG. 15.

FIGS. 15 and 16 illustrate the proximal cover 104 of the disposable portion 14 of the medication delivery device 10. The proximal cover 104 includes a main body 114 that has a generally cylindrical shape. The main body 114 includes an inner passageway 116 that receives other components, including the biasing element 106 and the therapeutic agent delivery assembly 108 of the disposable portion 14 (both shown elsewhere) and the plunger 36 of the reusable portion 12 (shown elsewhere). An inner surface 118 of the proximal cover 104 carries a biasing platform 120 (illustratively, a radially-inwardly extending flange) that inhibits the therapeutic agent delivery assembly 108 from extending proximally through the inner passageway 116. The inner surface 118 also includes a coupling feature 122 (illustratively, a threaded surface) for coupling the proximal cover 104 to the housing 102 (shown elsewhere). An outer surface 124 of the proximal cover 104 also includes a plurality of securing features 126 for selectively coupling to the securing features 68 of the reusable portion 12 (shown elsewhere) and thereby selectively securing the disposable portion 14 to the reusable portion 12. The securing features 126 may provide a bayonet-like or "twist-to-lock" connector; more specifically, the securing features 126 may be generally L-shaped recesses. In other embodiments, different arrangements of the proximal cover 104 are possible. For example, the coupling feature 122 may be a welded connection to the housing 102.

Figure 17:
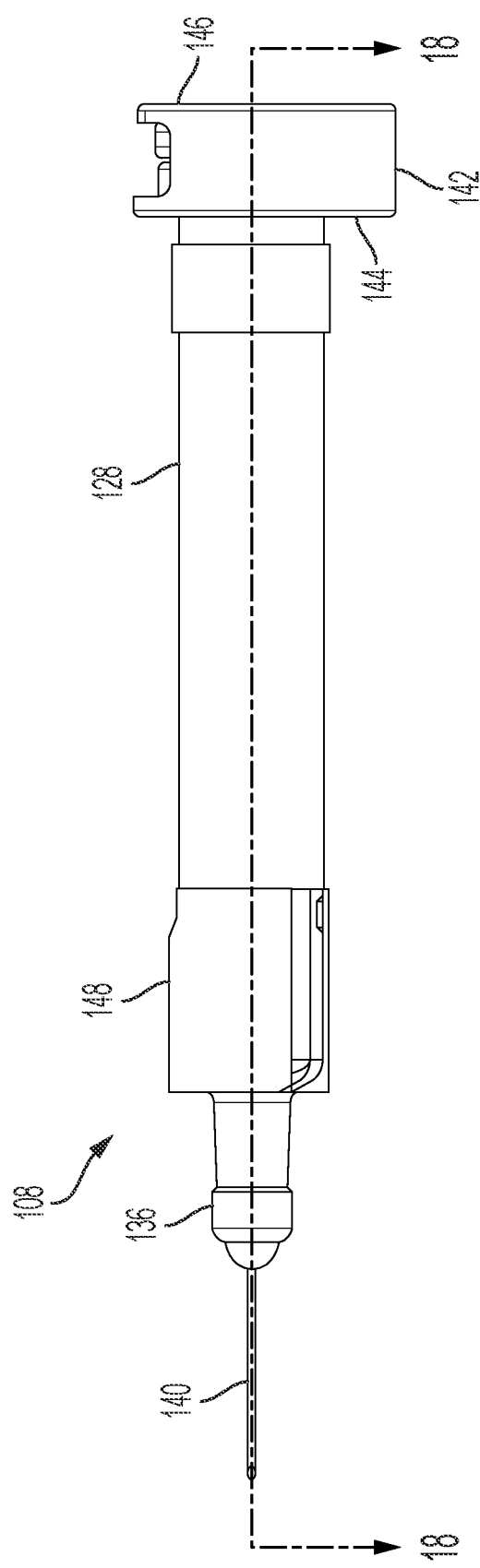
FIG. 17 is a side view of a therapeutic agent delivery assembly of the disposable portion of FIG. 13.
Figure 18:
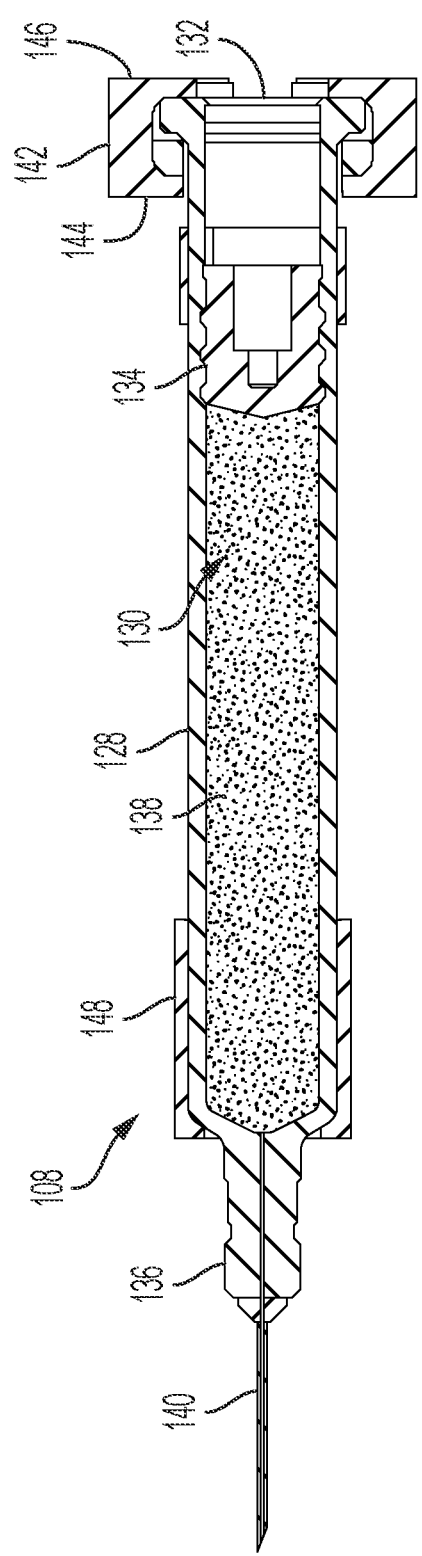
FIG. 18 is a longitudinal sectional view of the therapeutic agent delivery assembly along line 18-18 of FIG. 17.

FIGS. 17 and 18 illustrate the therapeutic agent delivery assembly 108 of the disposable portion 14 of the medication delivery device 10. The therapeutic agent delivery assembly 108 includes a syringe chamber 128, and the syringe chamber 128 includes a syringe passageway 130 that has a proximal opening 132. The proximal opening 132 receives the plunger 36 of the disposable portion 14 (shown elsewhere). The syringe passageway 130 carries a piston 134, and the piston 134 translates away from the proximal opening 132 and towards an outlet portion 136 of the therapeutic agent delivery assembly 108 when the plunger 36 is driven by the drive mechanism 22 of the reusable portion 12 (shown elsewhere). The syringe passageway 130 also carries the therapeutic agent 138 (illustratively, 1 mL of the therapeutic agent 138, although other volumes, including, for example, 0.5 mL, 1.5 mL, 1.75 mL, 2 mL, 2.25 mL, or 2.5 mL may alternatively be carried) between the piston 134 and the outlet portion 136, more specifically a needle 140. As such, translation of the piston 134 in the syringe passageway 130 causes the needle 140 to discharge the therapeutic agent 138 therefrom. The therapeutic agent delivery assembly 108 further includes a proximal stop element 142 (illustratively, a semi-annular ring) that is carried by the syringe chamber 128 adjacent to the proximal opening 132. The proximal stop element 142 includes a distal side 144 that abuts the biasing element 106 (shown elsewhere), and the biasing element 106 thereby urges an opposite proximal side 146 of the proximal stop element 142 to abut the biasing platform 120 of the proximal cover 104 (shown elsewhere). The therapeutic agent delivery assembly 108 further includes a distal stop element 148 (illustratively, a semi-annular sleeve) that is carried by the syringe chamber 128 adjacent to the outlet portion 136. The distal stop element 148 abuts the baseplate 110 (shown elsewhere) to limit distal translation of the therapeutic agent delivery assembly 108 relative to the baseplate 110. In other embodiments, different arrangements of the therapeutic agent delivery assembly 108 are possible. For example, the therapeutic agent delivery assembly 108 could be replaced by or include another type of therapeutic agent container, such as a bellows or bladder structure.

Medication delivery devices according to the present disclosure carry and dispense one or more therapeutic agents, which may also be referred to as medications or drugs. Such therapeutic agents 138 may include, for example, epinephrine, anesthetics, analgesics, steroids, insulins, insulin analogs, insulin derivatives, GLP-1 receptor agonists such as dulaglutide or liraglutide, glucagon, glucagon analogs, glucagon derivatives, gastric inhibitory polypetide (GIP), GIP analogs, GIP derivatives, combined GIP/GLP-1 agonists such as tirzepatide, oxyntomodulin analogs, oxyntomodulin derivatives, basal insulins, therapeutic antibodies, which may include IL-17A antagonist such as ixekizumab, calcitonin-gene related peptide anatagonist such as galcanezumab, IL-13 monoclonal antibody such as lebrikizumab, IL-23 antibody such as mirikizumab, IL-2 conjugate, PD-1 antibody agonist, ramucirumab or other cancer treatments, or any other therapeutic agent that is capable of delivery by devices according to the present disclosure.

Medication delivery devices according to the present disclosure are operated in a manner generally as described herein by a user (for example, a healthcare professional, a caregiver, or another person) to deliver one or more therapeutic agents to a patient (for example, another person or the user).

FIGS. 19 and 20 illustrate the housing 102 of the disposable portion 14 of the medication delivery device 10. The housing 102 includes a main body 150 that has a generally cylindrical shape that flares outwardly at the distal end 18. The main body 150 includes an inner passageway 152 that carries other components of the disposable portion 14, specifically the therapeutic agent delivery assembly 108, the biasing element 106, the baseplate 110, and the base portion 112 (all shown elsewhere). Adjacent to the inner passageway 152, an inner surface 154 of the housing 102 carries a biasing platform 156 (illustratively, a radially-inwardly extending flange) that abuts the biasing element 106 (shown elsewhere). As such, the housing 102 carries the biasing element 106 between the biasing platform 156 and the proximal stop element 142 of the therapeutic agent delivery assembly 108 (shown elsewhere). Externally and at a proximal end 158, the housing 102 further includes a coupling feature 160 (illustratively, a threaded surface) for coupling to the proximal cover 104 (shown elsewhere), and the proximal cover 104 retains the therapeutic agent delivery assembly 108 in the inner passageway 152 of the housing 102. In other embodiments, different arrangements of the housing 102 are possible. For example, the coupling feature 160 may be a welded connection to the proximal cover 104. As another example, the housing 102 may have a non-flaring shape at the distal end 18.

Figure 23:
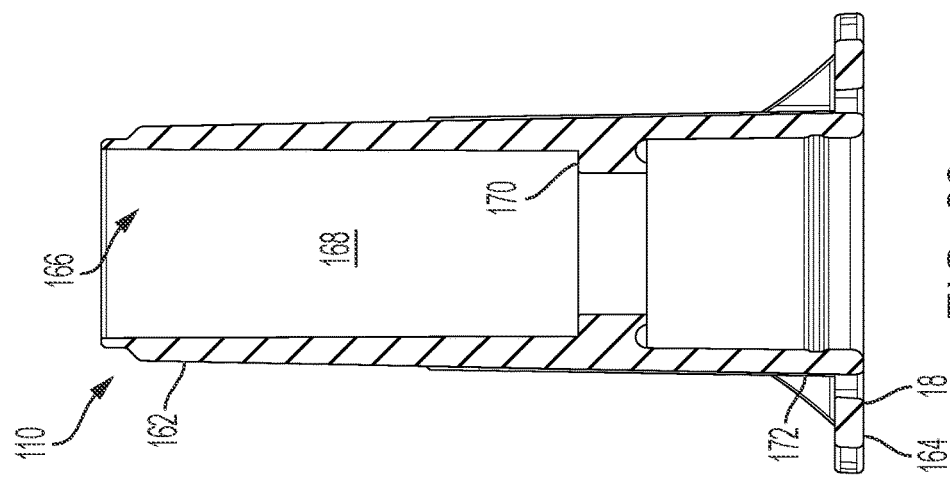
FIG. 23 is a longitudinal sectional view of the baseplate along line 23-23 of FIG. 22.
Figure 22:
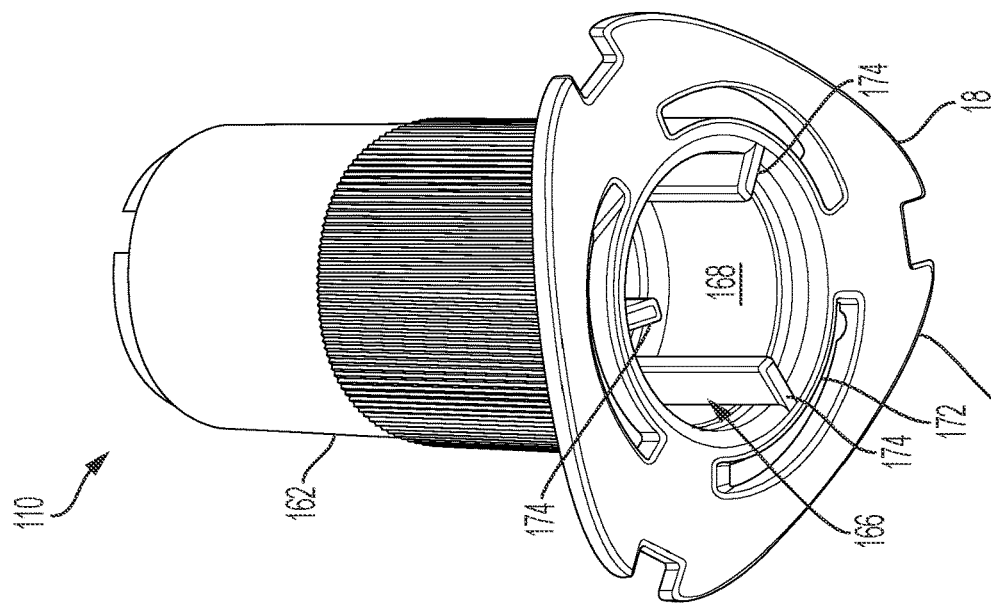
FIG. 22 is a bottom perspective view of the baseplate of FIG. 21.
Figure 21:
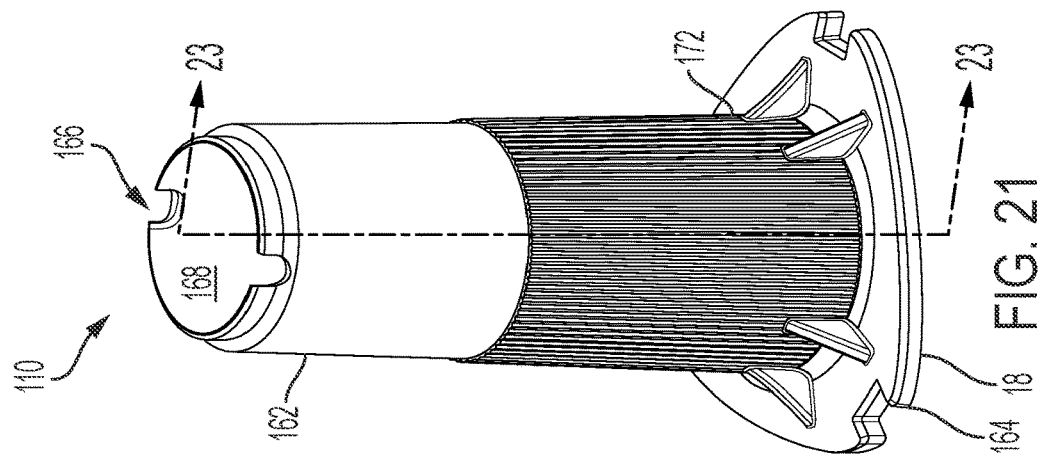
FIG. 21 is a top perspective view of a baseplate of the disposable portion of FIG. 13.

FIGS. 21-23 illustrate the baseplate 110 of the disposable portion 14 of the medication delivery device 10. The baseplate 110 includes a main body 162 that has a generally cylindrical shape with an outwardly extending flange 164 at the distal end 18. The main body 162 includes an inner passageway 166 that carries other components of the disposable portion 14, specifically the therapeutic agent delivery assembly 108 and the base portion 112 (both shown elsewhere). Adjacent to the inner passageway 166, an inner surface 168 of the baseplate 110 carries a stop element 170 (illustratively, a radially-inwardly extending flange) that abuts the distal stop element 148 of the therapeutic agent delivery assembly 108 (shown elsewhere) to limit distal translation of the therapeutic agent delivery assembly 108 relative to the baseplate 110. A distal portion 172 of the inner surface 168 also carries one or more guard features 174 (illustratively, a plurality of elongated ridges, more specifically three ridges) that inhibit objects (such as a fingertip of the user or patient) from entering the inner passageway 166 and contacting the needle 140 of the therapeutic agent delivery assembly 108 (shown elsewhere). In other embodiments, other arrangements of the baseplate 110 are possible. For example, the baseplate 110 may lack the outwardly extending flange 164 at the distal end 18.

Figure 24:
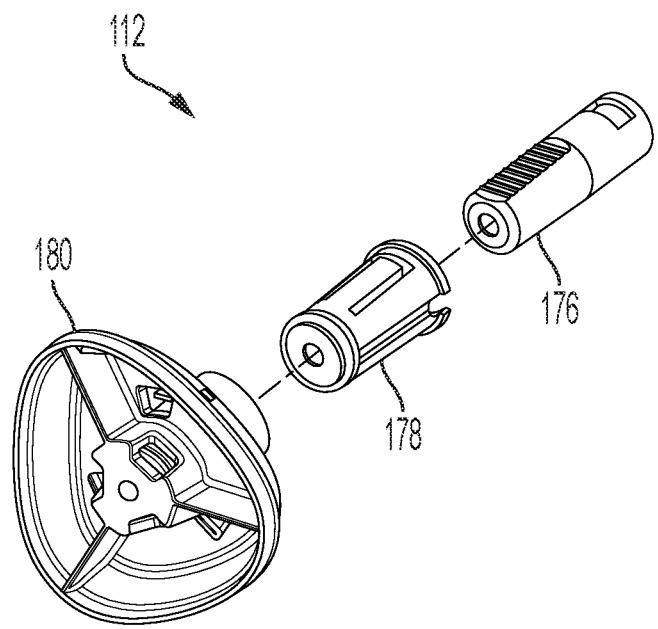
FIG. 24 is an exploded perspective view of a base portion of the disposable portion of FIG. 13.
Figure 25:
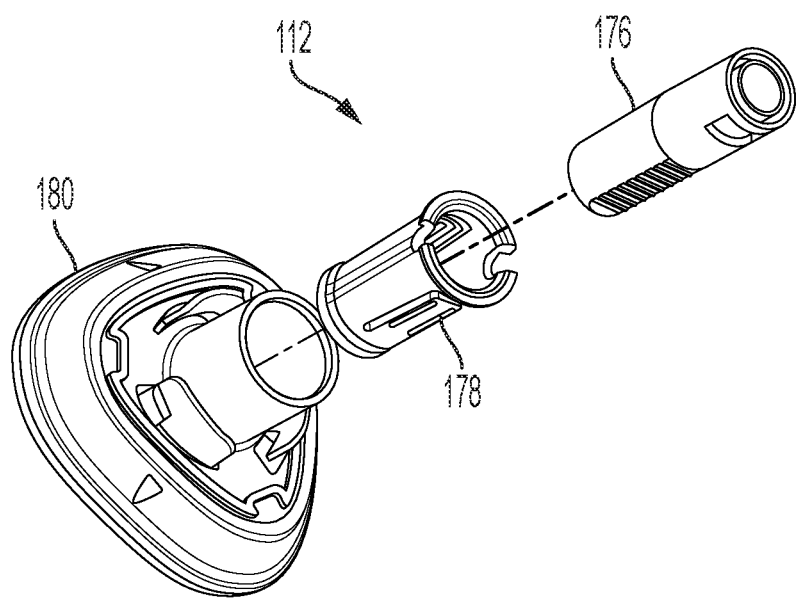
FIG. 25 is another exploded perspective view of the base portion of FIG. 24.

FIGS. 24 and 25 illustrate the base portion 112 of the disposable portion 14 of the medication delivery device 10. The base portion 112 is initially and detachably carried at the distal end 18 of the disposable portion 14. The base portion 112 includes a needle shield 176, which may also be referred to as a rigid needle shield, a shield puller 178, and a basecap 180. The needle shield 176 initially covers and maintains sterility of the needle 140 of the therapeutic agent delivery assembly 108 (shown elsewhere). The shield puller 178 couples the needle shield 176 to the basecap 180 and facilitates separating the needle shield 176 from the needle 140 upon detaching the basecap 180 from the housing 102 (shown elsewhere). The basecap 180 initially obscures the inner passageway 166 of the baseplate 110 (shown elsewhere) and retains the shield puller 178 and the needle shield 176 adjacent to the needle 140. The base portion 112 may be appropriate for use with a medication delivery device 10 carrying a specific volume of the therapeutic agent 138, such as 1 mL of the therapeutic agent 138. The base portion 112 or one or more components thereof, such as the puller 178 and the basecap 180, may alternatively have different features and/or dimensions, for example, for a medication delivery device 10 carrying a different volume of the therapeutic agent 138, such as 2 mL of the therapeutic agent 138.

Figure 26:
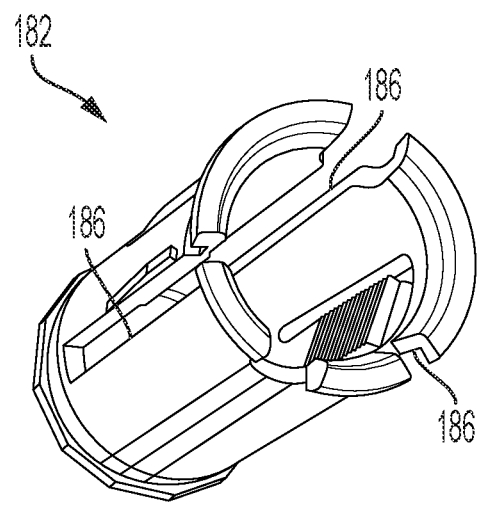
FIG. 26 is a perspective view of an alternative shield puller for the base portion of FIG. 24.
Figure 27:
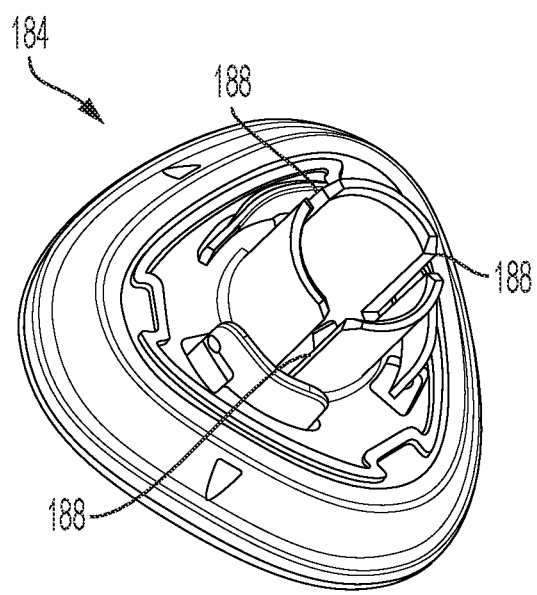
FIG. 27 is a perspective view of an alternative basecap for the base portion of FIG. 24.

In other embodiments, other arrangements of the base portion 112 are possible. For example, FIG. 26 illustrates an alternative shield puller 182 and FIG. 27 illustrates an alternative basecap 184 that may be used instead of the shield puller 178 and the basecap 180, respectively. The shield puller 182 and the basecap 184 include the same features as the shield puller 178 and the basecap 180, respectively, except that the shield puller 178 and the basecap 180 include guard-receiving features 186 and 188 that, as the name implies, receive the guard features 174 of the baseplate 110. Illustratively, the guard-receiving features 186 and 188 include a plurality of elongated slots for receiving the elongated ridges of the baseplate 110.

The medication delivery device 10 may include various alternative or additional features. For example, the medication delivery device 10 may include one or more features that facilitate unlocking the device 10. As a specific example, the device may include a second user input (not shown—for example, a button) that is actuatable by a user to unlock the device 10 and permit actuation of the first user input 26. Similarly, the device may include a second user input (not shown—for example, a button) that is actuatable by a user to activate or awaken the electronics assembly 96. As another specific example, the user input 26 may be a two-stage button that is initially depressed to unlock the device 10 and further depressed to actuate the device 10. As yet another example, the disposable portion 14 may include a sensor (not shown) that activates or awakens the electronics assembly 96 upon detecting that the distal end 18 is in contact with a patient. The electronics assembly 96 may include a wireless or wired connection for operatively coupling such a sensor to the electronic controller 98. As another specific example, the device 10 may include a cover (not shown) for inhibiting accidental actuation of the user input 26. In some embodiments, the device 10 may include one or more indicators (not shown) that change states to indicate that the device 10 is unlocked. For example, such indicators may include an electronic display or one or more LEDs, such as a yellow LED that illuminates to indicate that the device 10 is locked and a green LED that illuminates to indicate that the device 10 is unlocked.

As another example, the electronics assembly 96 may include various alternative or additional features. As a specific example, the first actuator 70 and/or the second actuator 72 may include sensors (not shown—for example, rotary encoder sensors) to facilitate monitoring and/or providing feedback for the positions of the frame 34 and/or the plunger 36, respectively. As another specific example, the electronics assembly 96 may include a sensor (not shown) for determining if the disposable portion 14 is coupled to the reusable portion 12. Such a sensor may activate or "awaken" the electronics assembly 96 upon detecting that the disposable portion 14 is coupled to the reusable portion 12. As yet another example, the disposable portion 14 may include an identifier (for example, an RFID transmitter or EEPROM) to facilitate providing properties of the therapeutic agent 138 to the reusable portion 12. Such properties may include, for example, the type and/or volume of the therapeutic agent 138 carried by the therapeutic agent delivery assembly 108. The reusable portion 12 may use the properties of the therapeutic agent 138 to determine, for example, an appropriate rate for driving the plunger 36 and delivering the therapeutic agent 138 to a patient.

Illustratively, a method of using the medication delivery device 10 is as follows. Referring to FIG. 28, the medication delivery device 10 is illustrated before coupling the disposable portion 14 to the reusable portion 12. The disposable portion 14 is coupled to the reusable portion 12 by coupling the securing features 126 of the disposable portion 14 to the securing features 68 of the reusable portion 12. More specifically, the disposable portion 14 is translated relative to the reusable portion 12 in a proximal direction D1 until the proximal cover 104 of the disposable portion 14 is received in the coupling portion 64 of the reusable portion 12, and then the disposable portion 14 is rotated relative to the reusable portion 12 in a rotational direction R1 to secure the L-shaped recesses of the proximal cover 104 to the L-shaped protrusions of the reusable portion 12. The medication delivery device 10 may be provided to a user before or after coupling the disposable portion 14 to the reusable portion 12.

Referring to FIG. 29, upon coupling the disposable portion 14 to the reusable portion 12, the device 10 occupies a "loaded" or "ready" configuration. In the ready configuration, the frame 34 of the drive mechanism 22 abuts the proximal stop element 142 of the therapeutic agent delivery assembly 108 and the plunger 36 abuts the piston 134 of the therapeutic agent delivery assembly 108. In addition, the base portion 112 obscures the needle 140, and the therapeutic agent delivery assembly 108 is disposed in a stowed configuration in which the needle 140 is disposed proximally relative to the distal end 18 of the device 10.

Figure 30:
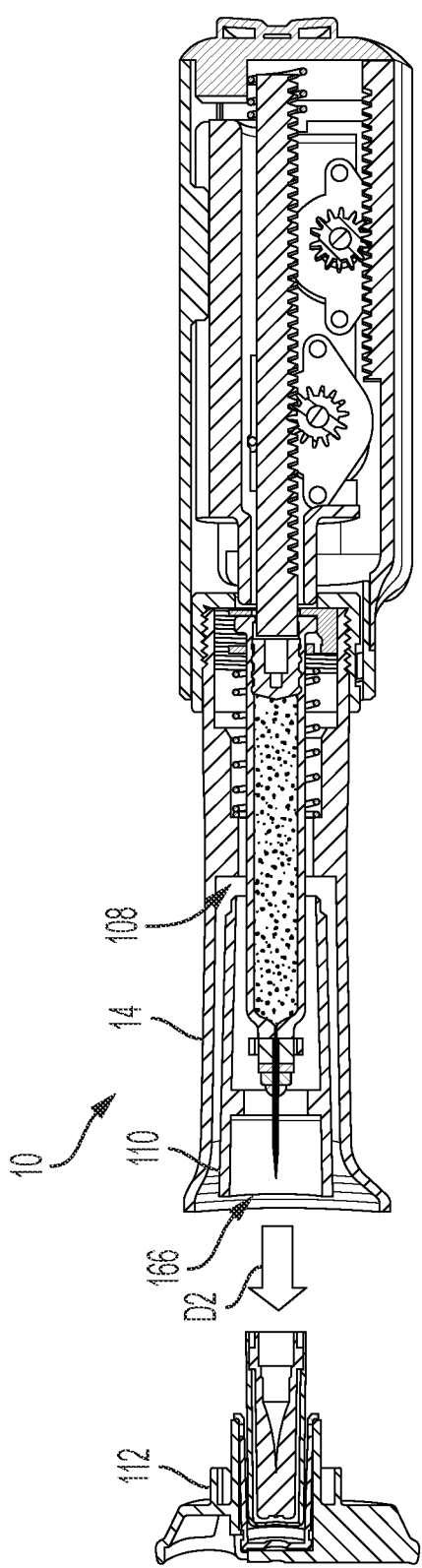
FIG. 30 is a longitudinal sectional view of the medication delivery device of FIG. 1 upon detaching the base portion from the disposable portion.

Referring to FIG. 30, the base portion 112 is next detached from the disposable portion 14. More specifically, the base portion 112 is translated relative to the disposable portion 14 in a distal direction D2. Upon detaching the base portion 112 from the disposable portion 14, the inner passageway 166 of the baseplate 110 is unobscured, but the therapeutic agent delivery assembly 108 remains in the stowed configuration.

Figure 31:
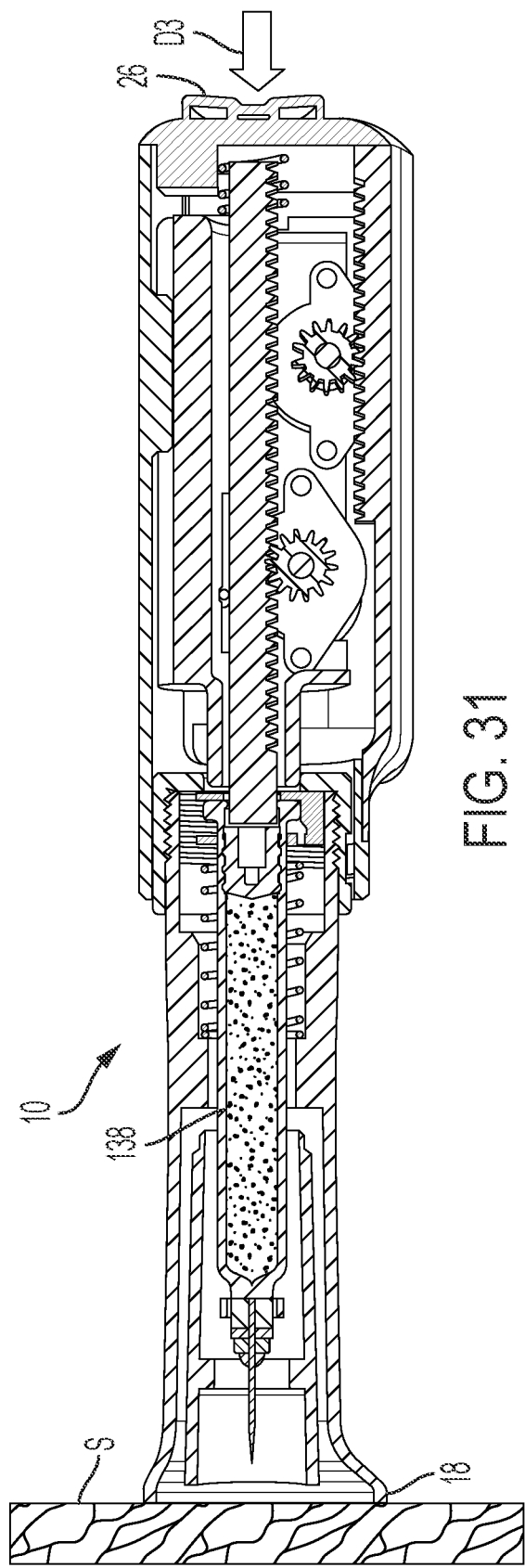
FIG. 31 is a longitudinal sectional view of the medication delivery device of FIG. 1 upon abutting the skin of a patient and actuating a user input of the device.

Referring to FIG. 31, the device 10 is then positioned such that the distal end 18 abuts the skin S of a patient. The user input 26 is next actuated (illustratively, depressed in a distal direction D3 for 3 seconds) to, generally, actuate the device 10 and deliver the therapeutic agent 138 to the patient.

Figure 32:
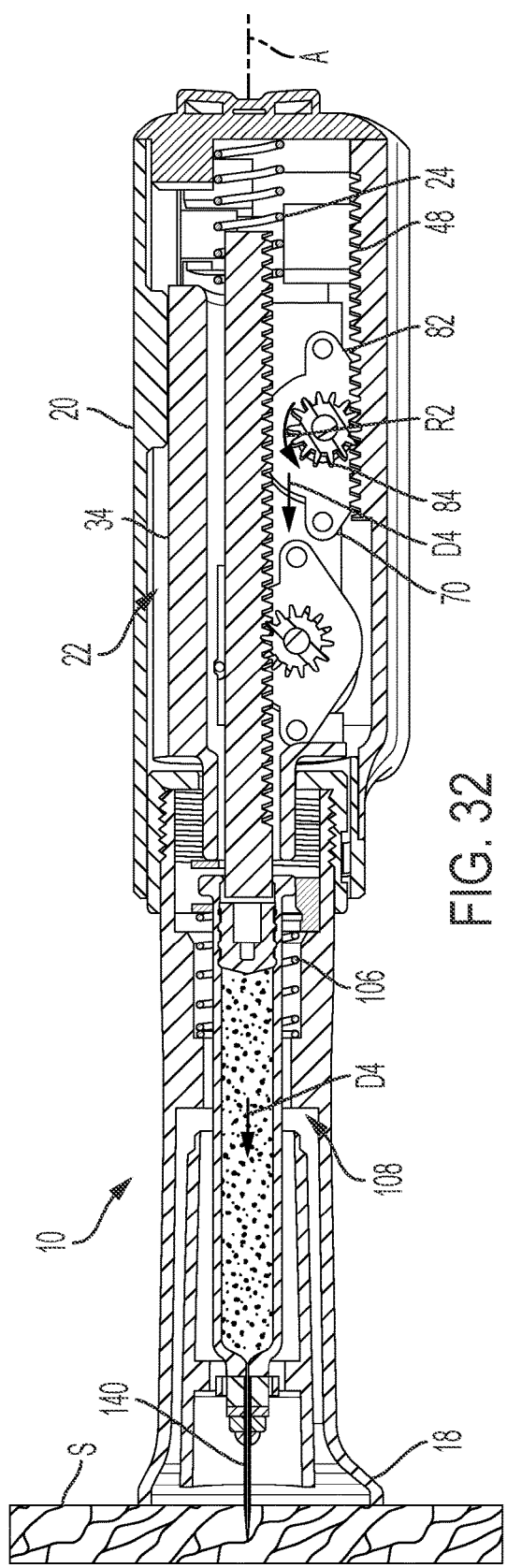
FIG. 32 is a longitudinal sectional view of the medication delivery device of FIG. 1 upon deploying a needle from the device and piercing the skin of the patient.

Referring to FIG. 32, the electronic controller 98 (shown elsewhere) energizes the first actuator 70 to distally advance the needle 140. More specifically, the electronic controller 98 energizes the first motor 82, and the first motor 82 rotatably drives the first pinion 84 in a rotational direction R2. The driving engagement of the first pinion 84 with the first rack 48 causes the drive mechanism 22 to translate relative to the housing 20 in a distal, first drive direction D4. As illustrated, the first drive direction D4 may be substantially parallel to the longitudinal axis A (that is, parallel ±5 degrees). The biasing element 24 may expand to assist translating the drive mechanism 22 relative to the housing 20 in the first drive direction D4. The frame 34 of the drive mechanism 22 pushes the therapeutic agent delivery assembly 108 in the first drive direction D4 and compresses the biasing element 106. The therapeutic agent delivery assembly 108 thereby moves from the stowed configuration to a deployed configuration. In the deployed configuration, the needle 140 at least partially extends distally from the distal end 18 of the device 10 and pierces the skin S of the patient.

Figure 33:
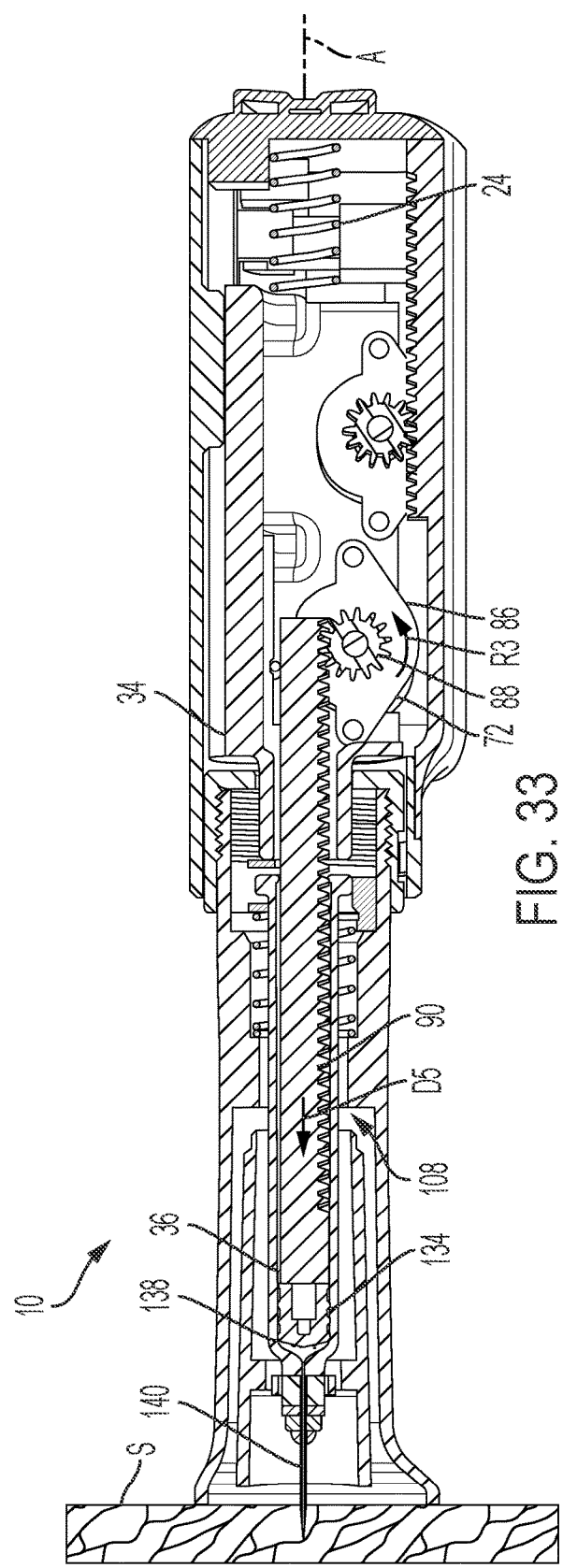
FIG. 33 is a longitudinal sectional view of the medication delivery device of FIG. 1 upon delivering a therapeutic agent to the patient via the needle.

Referring to FIG. 33, the electronic controller 98 (shown elsewhere) next energizes the second actuator 72 to deliver the therapeutic agent 138 to the patient. More specifically, the electronic controller 98 energizes the second motor 86, the second motor 86 rotatably drives the second pinion 88 in a rotation direction R3. The second pinion 88 translatably drives the second rack 90 and the plunger 36 relative to the frame 34 in a distal, second drive direction D5. As illustrated, the second drive direction D5 may be substantially parallel to the longitudinal axis A (that is, parallel ±5 degrees). The plunger 36 pushes the piston 134 of the therapeutic agent delivery assembly 108 in the second drive direction D5. The piston 134 thereby pushes the therapeutic agent 138 distally to the needle 140, and the needle 140 delivers the therapeutic agent 138 to the patient.

Referring to FIG. 34, the electronic controller 98 (shown elsewhere) then energizes the first actuator 70 to proximally retract the needle 140. More specifically, the electronic controller 98 energizes the first motor 82, and the first motor 82 rotatably drives the first pinion 84 in a rotational direction R4. The driving engagement of the first pinion 84 with the first rack 48 causes the drive mechanism 22 to translate relative to the housing 20 in a proximal, first retraction direction D6. As illustrated, the first retraction direction D6 may be substantially parallel to the longitudinal axis A (that is, parallel ±5 degrees). This motion of the drive mechanism 22 permits the biasing element 106 to expand and translate the therapeutic agent delivery assembly 108 in the first retraction direction D6. The therapeutic agent delivery assembly 108 thereby moves from the deployed configuration to a retracted configuration. In the retracted configuration, the needle 140 is withdrawn from the skin S of the patient and is disposed proximally relative to the distal end 18 of the device 10.

Referring to FIG. 35, the electronic controller 98 (shown elsewhere) next energizes the second actuator 72 to retract the plunger 36 from the therapeutic agent delivery assembly 108. More specifically, the electronic controller 98 energizes the second motor 86, the second motor 86 rotatably drives the second pinion 88 in a rotation direction R5. The second pinion 88 translatably drives the second rack 90 and the plunger 36 relative to the frame 34 in a proximal, second retraction direction D7. As illustrated, the second retraction direction D7 may be substantially parallel to the longitudinal axis A (that is, parallel ±5 degrees). The device 10 may be moved away from the skin S of the patient before or after retracting the plunger 36.

Figure 36:
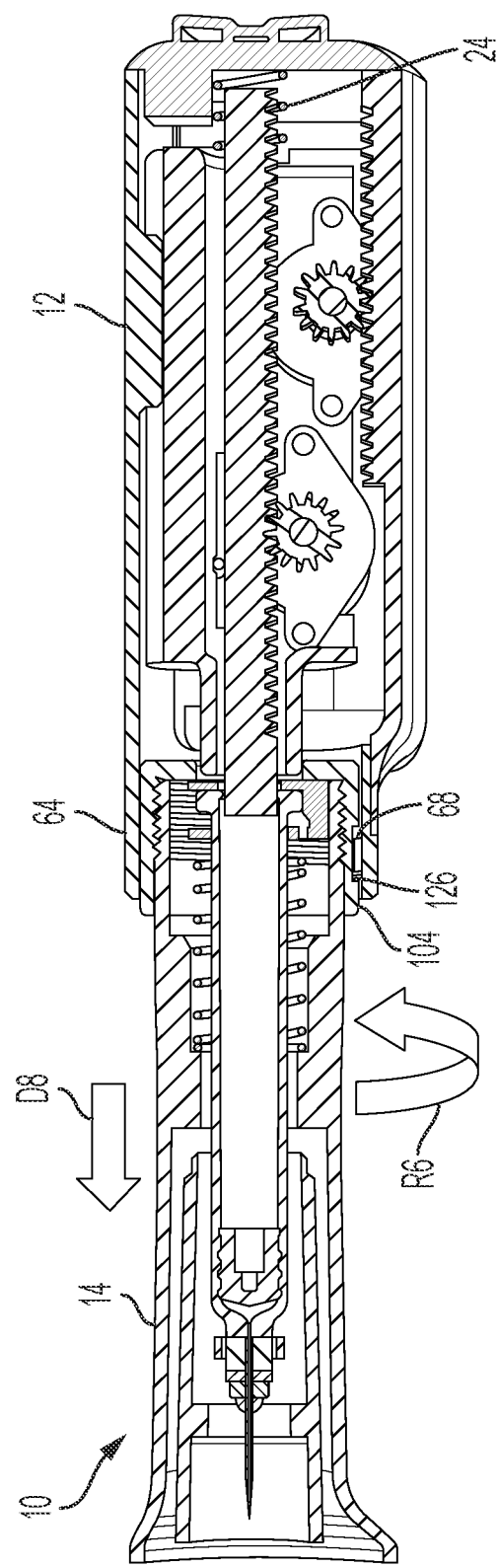
FIG. 36 is a longitudinal sectional view of the medication delivery device of FIG. 1 while detaching the disposable portion from the reusable portion.

Referring to FIG. 36, the disposable portion 14 may then be detached from the reusable portion 12. The disposable portion 14 is detached from the reusable portion 12 by uncoupling the securing features 126 of the disposable portion 14 from the securing features 68 of the reusable portion 12. More specifically, the disposable portion 14 is rotated relative to the reusable portion 12 in a rotational direction R6 to disengage the L-shaped recesses of the proximal cover 104 from the L-shaped protrusions of the reusable portion 12, and then the disposable portion 14 is translated relative to the reusable portion 12 in a distal direction D8 until the proximal cover 104 of the disposable portion 14 is detached from the coupling portion 64 of the reusable portion 12.

Figure 37:
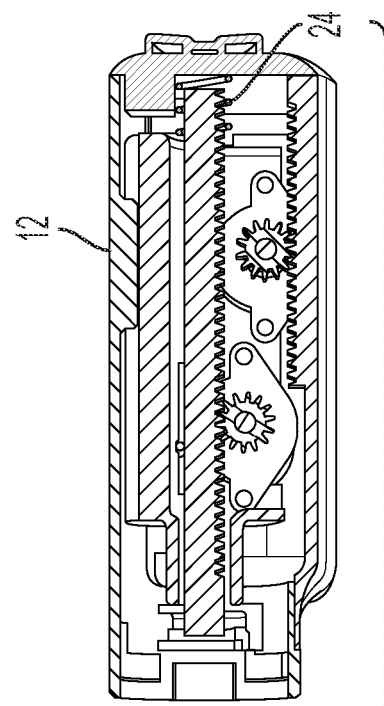
FIG. 37 is a partial longitudinal sectional view of the medication delivery device of FIG. 1 after detaching the disposable portion from the reusable portion.
Figure 37:
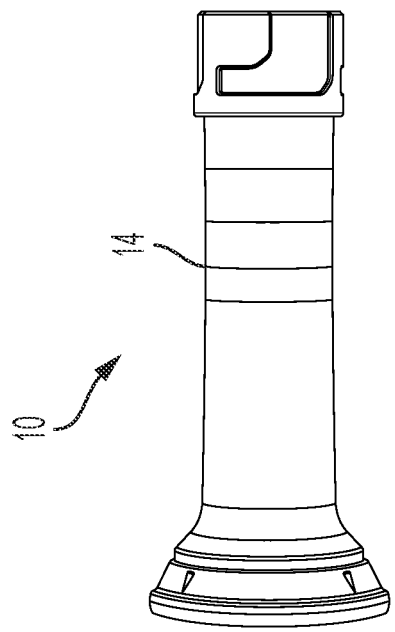

Referring to FIG. 37, upon detaching the spent disposable portion 14 from the reusable portion 12, the spent disposable portion 14 may be discarded, and the method of using the device 10 may be repeated with a fresh disposable portion 14.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

Various aspects are described in this disclosure, which include, but are not limited to, the following aspects:

1. A medication delivery device, including: a disposable portion, including: a housing having a distal end; a therapeutic agent delivery assembly carried by the housing, the therapeutic agent delivery assembly including: a chamber including a passageway to carry a therapeutic agent; a needle in communication with the passageway; the therapeutic agent delivery assembly being translatable relative to the housing from a stowed configuration to a deployed configuration, in the stowed configuration the needle being disposed proximally relative to the distal end of the housing, and in the deployed configuration the needle at least partially extending distally from the distal end of the housing; a reusable portion detachably carrying the disposable portion, the reusable portion including: a housing; a drive mechanism carried by the housing of the reusable portion, the drive mechanism including: a first rack and pinion mechanism; a frame translatably carried by the housing of the reusable portion via the first rack and pinion mechanism; a second rack and pinion mechanism coupled to the frame; a plunger translatably carried by the frame via the second rack and pinion mechanism; the first rack and pinion mechanism being actuatable to translate the frame relative to the housing of the reusable portion, the frame thereby translating the therapeutic agent delivery assembly relative to the housing of the disposable portion from the stowed configuration to the deployed configuration, and the second rack and pinion mechanism being actuatable to translate the plunger relative to the frame to deliver the therapeutic agent from the needle.
2. The medication delivery device of aspect 1, wherein the medication delivery device is elongated along a longitudinal axis extending between the disposable portion and the reusable portion, the first rack and pinion mechanism is actuatable to translate the frame relative to the housing of the reusable portion in a drive direction, the drive direction being substantially parallel to the longitudinal axis, and the frame thereby translating the therapeutic agent delivery assembly relative to the housing of the disposable portion in the drive direction and from the stowed configuration to the deployed configuration.
3. The medication delivery device of aspect 2, wherein the drive direction is a first drive direction, and wherein the second rack and pinion mechanism is actuatable to translate the plunger relative to the frame in a second drive direction, the second drive direction being substantially parallel to the longitudinal axis, and the plunger thereby causing the therapeutic agent delivery assembly to deliver the therapeutic agent from the needle.
4. The medication delivery device of aspect 1, wherein the medication delivery device is elongated along a longitudinal axis extending between the disposable portion and the reusable portion, the second rack and pinion mechanism is actuatable to translate the plunger relative to the frame in a drive direction, the drive direction being substantially parallel to the longitudinal axis, and the plunger thereby causing the therapeutic agent delivery assembly to deliver the therapeutic agent from the needle.
5. The medication delivery device of any one of aspects 1-4, wherein the first rack and pinion mechanism includes: a motor carried by the frame; a pinion rotatably driven by the motor; and a rack carried by the housing of the reusable portion and translatably driven by the pinion.
6. The medication delivery device of aspect 5, wherein the rack is monolithically formed with the housing of the reusable portion.
7. The medication delivery device of aspect 5, wherein the motor is a first motor, the pinion is a first pinion, and the rack is a first rack, and wherein the second rack and pinion mechanism includes: a second motor carried by the frame; a second pinion rotatably driven by the second motor; and a second rack carried by the plunger and translatably driven by the second pinion.
8. The medication delivery device of any one of aspects 1-7, wherein the second rack and pinion mechanism includes: a motor carried by the frame; a pinion rotatably driven by the motor; and a rack carried by the plunger and translatably driven by the pinion.
9. The medication delivery device of aspect 8, wherein the rack is monolithically formed with the plunger.
10. The medication delivery device of any one of aspects 1-9, wherein the therapeutic agent delivery assembly is translatable relative to the housing of the disposable portion from the deployed configuration to a retracted configuration, in the retracted configuration the needle being disposed proximally relative to the distal end of the housing of the disposable portion, wherein the first rack and pinion mechanism is actuatable to translate the frame relative to the housing of the reusable portion in a retraction direction, and wherein the therapeutic agent delivery assembly further includes a biasing element, the biasing element elongating when the first rack and pinion mechanism translates the frame relative to the housing of the reusable portion in the retraction direction, and the biasing element thereby translating the therapeutic agent delivery assembly relative to the housing of the disposable portion from the deployed configuration to the retracted configuration.
11. The medication delivery device of any one of aspects 1-10, wherein the second rack and pinion mechanism is actuatable to translate the plunger relative to the frame in a drive direction, the plunger thereby causing the therapeutic agent delivery assembly to deliver the therapeutic agent from the needle, and wherein the second rack and pinion mechanism is further actuatable to translate the plunger relative to the frame in a retraction direction, the retraction direction being opposite the drive direction.
12. The medication delivery device of any one of aspects 1-11, wherein the passageway of the chamber includes a therapeutic agent.
13. A method for delivering a therapeutic agent from a medication delivery device to a patient, the medication delivery device including a reusable portion and a disposable portion detachably carried by the reusable portion, the disposable portion carrying the therapeutic agent, the method including: positioning a distal end of the disposable portion adjacent to the skin of the patient, a needle of the disposable portion being disposed proximally relative to the distal end of the disposable portion; actuating a first rack and pinion mechanism of the reusable portion to thereby drive the needle relative to the distal end of the disposable portion such that the needle at least partially extends distally from the distal end of the disposable portion and pierces the skin of the patient; and actuating a second rack and pinion mechanism of the reusable portion to thereby cause the disposable portion to deliver the therapeutic agent from the needle to the patient.
14. The method of aspect 13, wherein actuating the first rack and pinion mechanism of the reusable portion to thereby drive the needle relative to the distal end includes driving the needle in a drive direction, and further including, after actuating the second rack and pinion mechanism of the reusable portion, actuating the first rack and pinion mechanism of the reusable portion to thereby drive the needle relative to the distal end of the disposable portion in a retraction direction such that the needle retracts from the skin of the patient.
15. The method of aspect 14, wherein the disposable portion is a first disposable portion and the therapeutic agent is a first therapeutic agent, the method further including: after actuating the second rack and pinion mechanism of the reusable portion a second time after delivering the first therapeutic agent from the needle to the patient, detaching the first disposable portion from the reusable portion; and attaching a second disposable portion to the reusable portion, the second disposable portion carrying a second therapeutic agent.
16. The method of aspect 14, wherein: actuating the first rack and pinion mechanism to drive the needle includes rotating a first pinion in a first direction; actuating the second rack and pinion mechanism to deliver the therapeutic agent from the needle includes rotating a second pinion in a second direction; the method further including: actuating the first rack and pinion mechanism to retract the needle by rotating the first pinion in a third direction opposite the first direction; and actuating the second rack and pinion mechanism to retract a plunger of the reusable portion from the disposable portion by rotating the second pinion in a fourth direction opposite the second direction.
17. A disposable portion for a medication delivery device, the medication delivery device including a reusable portion configured to detachably carry the disposable portion, the disposable portion including: a housing having a distal end; a therapeutic agent delivery assembly translatably carried in the housing, the therapeutic agent delivery assembly including: a chamber including a passageway; a therapeutic agent carried in the passageway; a needle in communication with the passageway; a biasing element carried in the housing, the biasing element biasing the therapeutic agent delivery assembly toward a stowed configuration, in the stowed configuration the needle being disposed proximally relative to the distal end of the housing; and a proximal cover carried by the housing, the proximal cover retaining the therapeutic agent delivery assembly in the housing, and the proximal cover including a securing feature configured to detachably secure the disposable portion to the reusable portion; the therapeutic agent delivery assembly being translatable by the reusable portion relative to the housing from the stowed configuration to a deployed configuration, in the deployed configuration the needle at least partially extending distally from the distal end of the housing.
18. The disposable portion of aspect 17, wherein the securing feature of the proximal cover includes a twist-to-lock connector.
19. The disposable portion of any one of aspects 17-18, wherein the proximal cover includes an inner passageway, the inner passageway being configured to receive a plunger of the reusable portion and permit the plunger to translate the therapeutic agent delivery assembly from the stowed configuration to the deployed configuration.
20. The disposable portion of any one of aspects 17-19, further including a baseplate carried by the housing, the baseplate including an inner passageway that receives the therapeutic agent delivery assembly, and the baseplate further including a guard feature configured to inhibit entry of foreign objects into the inner passageway.
21. The disposable portion of aspect 20, wherein the guard feature includes an elongated ridge.
22. The disposable portion of any one of aspects 17-21, wherein the proximal cover is weldably connected to the housing.
23. A drive portion of a medication delivery device including: a housing; a drive mechanism carried by the housing, the drive mechanism including: a first rack and pinion mechanism; a frame translatably carried by the housing via the first rack and pinion mechanism; a second rack and pinion mechanism coupled to the frame; a plunger translatably carried by the frame via the second rack and pinion mechanism; the first rack and pinion mechanism being actuatable to translate the frame relative to the housing configured to translate a therapeutic agent delivery assembly from a stowed configuration to a deployed configuration, and the second rack and pinion mechanism being actuatable to translate the plunger relative to the frame to deliver a therapeutic agent from a needle of the therapeutic agent delivery assembly.
24. The drive portion of aspect 23, wherein the first rack and pinion mechanism includes: a motor carried by the frame; a pinion rotatably driven by the motor; and a rack carried by the housing of the reusable portion and translatably driven by the pinion.
25. The drive portion of aspect 24, wherein the rack is monolithically formed with the housing of the reusable portion.
26. The drive portion of any one of aspects 23-25, wherein the motor is a first motor, the pinion is a first pinion, and the rack is a first rack, and wherein the second rack and pinion mechanism includes: a second motor carried by the frame; a second pinion rotatably driven by the second motor; and a second rack carried by the plunger and translatably driven by the second pinion.
27. The drive portion of aspect 26, wherein the second rack and pinion mechanism includes: a motor carried by the frame; a pinion rotatably driven by the motor; and a rack carried by the plunger and translatably driven by the pinion.
28. The drive portion of aspect 27, wherein the rack is monolithically formed with the plunger.

We claim:
1. A medication delivery device, comprising:
 a disposable portion, comprising:
  a housing having a distal end;
  a therapeutic agent delivery assembly carried by the housing of the disposable portion, the therapeutic agent delivery assembly comprising:
   a chamber comprising a passageway to carry a therapeutic agent;
   a needle in communication with the passageway;
  the therapeutic agent delivery assembly being translatable relative to the housing of the disposable portion from a stowed configuration to a deployed configu- ration, in the stowed configuration the needle being disposed proximally relative to the distal end of the housing of the disposable portion, and in the deployed configuration the needle at least partially extending distally from the distal end of the housing of the disposable portion;
a reusable portion detachably carrying the disposable portion, the reusable portion comprising:
a housing;
a drive mechanism carried by the housing of the reusable portion, the drive mechanism comprising:
a first rack and pinion mechanism;
a frame translatably carried by the housing of the reusable portion via the first rack and pinion mechanism;
a second rack and pinion mechanism coupled to the frame;
a plunger translatably carried by the frame via the second rack and pinion mechanism;
the first rack and pinion mechanism being actuatable to translate the frame relative to the housing of the reusable portion, the frame thereby translating the therapeutic agent delivery assembly relative to the housing of the disposable portion from the stowed configuration to the deployed configuration, and the second rack and pinion mechanism being actuatable to translate the plunger relative to the frame to deliver the therapeutic agent from the needle.

2. The medication delivery device of claim 1, wherein the medication delivery device is elongated along a longitudinal axis extending between the disposable portion and the reusable portion, the first rack and pinion mechanism is actuatable to translate the frame relative to the housing of the reusable portion in a drive direction, the drive direction being substantially parallel to the longitudinal axis, and the frame thereby translating the therapeutic agent delivery assembly relative to the housing of the disposable portion in the drive direction and from the stowed configuration to the deployed configuration.

3. The medication delivery device of claim 2, wherein the drive direction is a first drive direction, and wherein the second rack and pinion mechanism is actuatable to translate the plunger relative to the frame in a second drive direction, the second drive direction being substantially parallel to the longitudinal axis, and the plunger thereby causing the therapeutic agent delivery assembly to deliver the therapeutic agent from the needle.

4. The medication delivery device of claim 1, wherein the medication delivery device is elongated along a longitudinal axis extending between the disposable portion and the reusable portion, the second rack and pinion mechanism is actuatable to translate the plunger relative to the frame in a drive direction, the drive direction being substantially parallel to the longitudinal axis, and the plunger thereby causing the therapeutic agent delivery assembly to deliver the therapeutic agent from the needle.

5. The medication delivery device of claim 1, wherein the first rack and pinion mechanism comprises:
a motor carried by the frame;
a pinion rotatably driven by the motor; and
a rack carried by the housing of the reusable portion and translatably driven by the pinion.

6. The medication delivery device of claim 5, wherein the rack is monolithically formed with the housing of the reusable portion.

7. The medication delivery device of claim 5, wherein the motor is a first motor, the pinion is a first pinion, and the rack is a first rack, and wherein the second rack and pinion mechanism comprises:
a second motor carried by the frame;
a second pinion rotatably driven by the second motor; and
a second rack carried by the plunger and translatably driven by the second pinion.

8. The medication delivery device of claim 1, wherein the second rack and pinion mechanism comprises:
a motor carried by the frame;
a pinion rotatably driven by the motor; and
a rack carried by the plunger and translatably driven by the pinion.

9. The medication delivery device of claim 8, wherein the rack is monolithically formed with the plunger.

10. The medication delivery device of claim 1, wherein the therapeutic agent delivery assembly is translatable relative to the housing of the disposable portion from the deployed configuration to a retracted configuration, in the retracted configuration the needle being disposed proximally relative to the distal end of the housing of the disposable portion, wherein the first rack and pinion mechanism is actuatable to translate the frame relative to the housing of the reusable portion in a retraction direction, and wherein the therapeutic agent delivery assembly further comprises a biasing element, the biasing element elongating when the first rack and pinion mechanism translates the frame relative to the housing of the reusable portion in the retraction direction, and the biasing element thereby translating the therapeutic agent delivery assembly relative to the housing of the disposable portion from the deployed configuration to the retracted configuration.

11. The medication delivery device of claim 1, wherein the second rack and pinion mechanism is actuatable to translate the plunger relative to the frame in a drive direction, the plunger thereby causing the therapeutic agent delivery assembly to deliver the therapeutic agent from the needle, and wherein the second rack and pinion mechanism is further actuatable to translate the plunger relative to the frame in a retraction direction, the retraction direction being opposite the drive direction.

12. The medication delivery device of claim 1, wherein the passageway of the chamber includes a therapeutic agent.

13. A drive portion of a medication delivery device comprising: a housing; a drive mechanism carried by the housing, the drive mechanism comprising: a first rack and pinion mechanism; a frame translatably carried by the housing via the first rack and pinion mechanism; a second rack and pinion mechanism coupled to the frame; a plunger translatably carried by the frame via the second rack and pinion mechanism; the first rack and pinion mechanism being actuatable to translate the frame relative to the housing and to translate a therapeutic agent delivery assembly from a stowed configuration to a deployed configuration, and the second rack and pinion mechanism being actuatable to translate the plunger relative to the frame to deliver a therapeutic agent from a needle of the therapeutic agent delivery assembly.

14. The drive portion of claim 13, wherein the first rack and pinion mechanism comprises: a motor carried by the frame; a pinion rotatably driven by the motor; and a rack carried by the housing of the reusable portion and translatably driven by the pinion.

15. The drive portion of claim 14, wherein the rack is monolithically formed with the housing of the reusable portion.

16. The drive portion of claim 14, wherein the motor is a first motor, the pinion is a first pinion, and the rack is a first rack, and wherein the second rack and pinion mechanism comprises: a second motor carried by the frame; a second pinion rotatably driven by the second motor; and a second rack carried by the plunger and translatably driven by the second pinion.

17. The drive portion of claim 13, wherein the second rack and pinion mechanism comprises: a motor carried by the frame; a pinion rotatably driven by the motor; and a rack carried by the plunger and translatably driven by the pinion.

18. The drive portion of claim 17, wherein the rack is monolithically formed with the plunger.

19. A medication delivery device, comprising:
the drive portion of claim 13; and
a disposable portion including a disposable portion housing having a distal end, a therapeutic agent delivery assembly carried by the disposable portion housing, the therapeutic agent delivery assembly having a chamber comprising a passageway to carry a therapeutic agent, and a needle in communication with the passageway, wherein the therapeutic agent delivery assembly is coupled to the frame of the drive portion and is translatable relative to the disposable portion housing from a stowed configuration to a deployed configuration, in the stowed configuration the needle being disposed proximally relative to the distal end of the disposable portion housing, and in the deployed configuration the needle at least partially extending distally from the distal end of the disposable portion housing,
wherein the plunger defines a rack that is movable within the passageway to move a piston within the chamber.

20. The medication delivery device of claim 19, wherein therapeutic agent delivery assembly further comprises a stop element carried by the chamber.

\* \* \* \* \*